United States Patent
Kamps et al.

(10) Patent No.: US 7,381,786 B2
(45) Date of Patent: Jun. 3, 2008

(54) METHODS OF POLYMER PREPARATION USING POLYCYCLIC DIHYDROXY COMPOUNDS

(75) Inventors: Jan Henk Kamps, Bergen op Zoom (NL); Jan-Pleun Lens, Breda (NL); James A. Mahood, Evansville, IN (US); Arakali Srinivasarao Radhakrishna, Bangalore (IN); T. Tilak Raj, Bangalore (IN); Ravindra Vikram Singh, Utter Pradesh (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/693,314

(22) Filed: Mar. 29, 2007

(65) Prior Publication Data

US 2007/0260033 A1  Nov. 8, 2007

Related U.S. Application Data

(63) Continuation-in-part of application No. 11/261,720, filed on Oct. 28, 2005, now Pat. No. 7,208,620, and a continuation-in-part of application No. 11/261,279, filed on Oct. 28, 2005, now Pat. No. 7,326,763.

(51) Int. Cl.
  C08G 63/02 (2006.01)
  C07C 69/76 (2006.01)
  C07C 67/00 (2006.01)
(52) U.S. Cl. .......................... 528/272; 560/76; 560/96
(58) Field of Classification Search .................... None
  See application file for complete search history.

(56) References Cited

U.S. PATENT DOCUMENTS

| | | | |
|---|---|---|---|
| 4,277,600 A | 7/1981 | Mark et al. | |
| 7,208,620 B1 * | 4/2007 | Kamps et al. | 560/76 |
| 2007/0080343 A1 | 4/2007 | Heun et al. | |

FOREIGN PATENT DOCUMENTS

| | | |
|---|---|---|
| EP | 0238305 | 9/1987 |
| JP | 06-016800 | 1/1994 |

OTHER PUBLICATIONS

JP 06-016800; Publication Date: Jan. 25, 1994; Abstract Only; 1 page.

E.P. Kohler et al.; "The Addition Reactions of Certain Pentadienones II. Addition of Malonic Esters"; Pentadienones and Malonic Esters; May 1924; pp. 1267-1278.

Alex T. Rowland et al., "Saponification of Dimethyl cis-2,6-Diphenyl-4-oxocyclohexane-1,1-dicarboxylate. A Reinvestigation"; J. Org. Chem. 1982, 47, 301-306.

Enrique Comez-Bengoa et al.; Michael Reaction of Stabilized Carbon Nucleophiles Catalyzed by [RuH2(PPh3)4]; J. Am. Chem. Soc. 1996, 118, 8553-8565.

International Search Report for International Application No. PCT/US2006/041351, mailed Apr. 5, 2007, 3 pages.

* cited by examiner

Primary Examiner—Paul A Zucker

(57) ABSTRACT

Disclosed herein is a process for preparing a polymer comprising structural units derived from polycyclic dihydroxy compound having Formula (I),

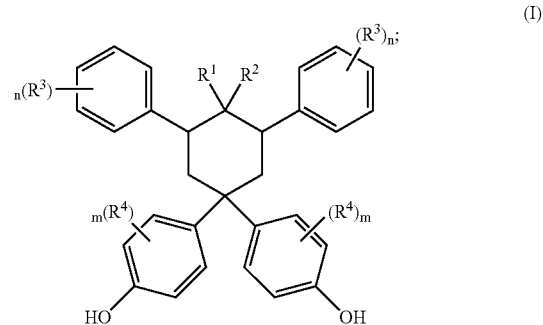

wherein $R^1$ is selected from the group consisting of a cyano functionality, a nitro functionality, an aliphatic functionality having 1 to 10 carbons, an aliphatic ester functionality having 2 to 10 carbons, a cycloaliphatic ester functionality having 4 to 10 carbons and an aromatic ester functionality having 4 to 10 carbons; $R^2$ is selected from the group consisting of a cyano functionality, a nitro functionality, an aliphatic ester functionality having 2 to 10 carbons, a cycloaliphatic ester functionality having 4 to 10 carbons and an aromatic ester functionality having 4 to 10 carbons; and each $R^3$ and $R^4$, at each occurrence, can be the same or different and are independently at each occurrence an aliphatic functionality having 1 to 10 carbons or a cycloaliphatic functionality having 3 to 10 carbons, "n" is an integer having a value 0 to 4 and "m" is an integer having a value 0 to 4. The process comprises subjecting a polycyclic dihydroxy compound of Formula (I) to polymerization.

22 Claims, No Drawings

METHODS OF POLYMER PREPARATION USING POLYCYCLIC DIHYDROXY COMPOUNDS

CROSS REFERENCE TO RELATED APPLICATIONS

This application is a continuation-in-part of U.S. patent application Ser. No. 11/261,720 filed on Oct. 28, 2005, now U.S. Pat. No. 7,208,630 issued on Apr. 24, 2007, and U.S. patent application Ser. No. 11/261,279 filed on Oct. 28, 2005, now U.S. Pat. No. 7,326,763 both of which are incorporated herein by reference.

BACKGROUND OF THE INVENTION

This disclosure relates to polycyclic dihydroxy compounds and polymers prepared using polycyclic dihydroxy compounds. More particularly the disclosure relates to polycyclic dihydroxy aromatic compounds, methods for preparing the compounds, polycarbonates prepared using polycyclic dihydroxy aromatic compounds, methods of preparing the polycarbonates, compositions comprising the polycarbonate, and uses thereof.

Polycyclic dihydroxy compounds are generally known to be useful in the preparation of polymers, particularly polycarbonates that exhibit exceptional properties like high glass transition temperature (Tg), high refractive index (RI), chemical resistance, and barrier properties. Materials having high Tg and high RI properties are in great demand for use in various applications like automotives and optical media.

Accordingly there remains a need in the art for new compounds and polymers made from these compounds. There is a need for polymers that have high Tg, high RI, or both, particularly for use in high temperature optical applications.

SUMMARY OF THE INVENTION

Disclosed herein is a process for preparing a polymer comprising structural units derived from polycyclic dihydroxy compound having Formula (I),

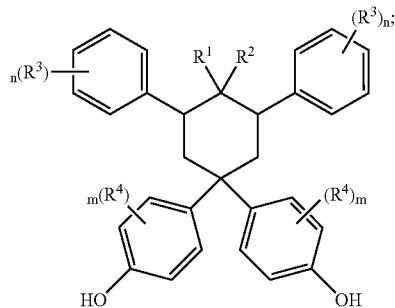

wherein $R^1$ is selected from the group consisting of a cyano functionality, a nitro functionality, an aliphatic functionality having 1 to 10 carbons, an aliphatic ester functionality having 2 to 10 carbons, a cycloaliphatic ester functionality having 4 to 10 carbons and an aromatic ester functionality having 4 to 10 carbons; $R^2$ is selected from the group consisting of a cyano functionality, a nitro functionality, an aliphatic ester functionality having 2 to 10 carbons, a cycloaliphatic ester functionality having 4 to 10 carbons and an aromatic ester functionality having 4 to 10 carbons; and each $R^3$ and $R^4$, at each occurrence, can be the same or different and are independently at each occurrence an aliphatic functionality having 1 to 10 carbons or a cycloaliphatic functionality having 3 to 10 carbons, "n" is an integer having a value 0 to 4 and "m" is an integer having a value 0 to 4. The process comprises subjecting a polycyclic dihydroxy compound of Formula (I) to polymerization.

The above-described and other features are exemplified by the following detailed description.

DETAILED DESCRIPTION OF THE INVENTION

Disclosed herein are polycyclic dihydroxy compounds and methods for preparing these compounds. Also disclosed herein are polymers prepared using these polycylic dihydroxy compounds and method of making the polymers.

The singular forms "a", "an" and "the" include plural referents unless the context clearly dictates otherwise. All ranges disclosed herein are inclusive and combinable (for example ranges of "up to 25 wt %, with 5 wt % to 20 wt % desired," is inclusive of the endpoints and all intermediate values of the ranges of "5 wt % to 25 wt %").

The modifier "about" used in connection with a quantity is inclusive of the stated value and has the meaning dictated by the context (for example, includes the degree of error associated with measurement of the particular quantity).

Cycloaliphatic ester functionality, as used herein, designates a cycloaliphatic functionality attached to a ester functionality, for example, cycloaliphatic-OC(O)—. Unless otherwise specified, the term "cycloaliphatic functionality" designates cyclic aliphatic functionalities having a valence of at least one, and comprising an array of atoms which is cyclic but which is not aromatic. A "cycloaliphatic functionality" may comprise one or more noncyclic components. For example, a cyclohexylmethyl group ($C_6H_{11}CH_2$—) is a cycloaliphatic functionality which comprises a cyclohexyl ring (the array of atoms which is cyclic but which is not aromatic) and a methylene group (the noncyclic component). The cycloaliphatic functionality may include heteroatoms such as nitrogen, sulfur, selenium, silicon and oxygen, or may be composed exclusively of carbon and hydrogen. For convenience, the term "cycloaliphatic functionality" is defined herein to encompass a wide range of functional groups such as alkyl groups, alkenyl groups, alkynyl groups, haloalkyl groups, conjugated dienyl groups, alcohol groups, ether groups, carboxylic acid groups, acyl groups (for example carboxylic acid derivatives such as esters and amides), amine groups and nitro groups. For example, the 4-methylcyclopent-1-yl group is a $C_6$ cycloaliphatic functionality comprising a methyl group, wherein the methyl group is a functional group which is an alkyl group. Similarly, the 2-nitrocyclobut-1-yl group is a $C_4$ cycloaliphatic functionality comprising a nitro group, wherein the nitro group is a functional group. A cycloaliphatic functionality may comprise one or more halogen atoms which may be the same or different. Halogen atoms include, for example, fluorine, chlorine, bromine, and iodine. Exemplary cycloaliphatic functionalities comprise cyclopropyl, cyclobutyl, 1,1,4,4-tetramethylcyclobutyl, piperidinyl, 2,2,6,6-tetramethylpiperydinyl and cyclohexyl, cyclopentyl.

As used herein, the term "aromatic ester functionality" refers to an array of atoms having a valence of at least one comprising at least one aromatic group attached to a ester functionality, for example, aromatic group-OC(O)—. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic functionality" includes but is not limited to phenyl, pyridyl, furanyl, thienyl, naphthyl, phenylene, and biphenyl functionalities. The aromatic functionality may also include nonaromatic components. For example, a benzyl group is an aromatic functionality that comprises a phenyl ring (the aromatic group) and a methylene group (the nonaromatic component). Similarly a tetrahydronaphthyl functionality is an aromatic functionality comprising an aromatic group ($C_6H_3$) fused to a nonaromatic component —$(CH_2)_4$—. For convenience, the term "aromatic functionality" is defined herein to encompass a wide range of functional groups such as alkyl groups, haloalkyl groups, haloaromatic groups, alcohol groups, ether groups, carboxylic acid groups, acyl groups (for example carboxylic acid derivatives such as esters and amides), amine groups and nitro groups. For example, the 4-methylphenyl functionality is a $C_7$ aromatic functionality comprising a methyl group, wherein the methyl group is a functional group which is an alkyl group. Similarly, the 2-nitrophenyl group is a $C_6$ aromatic functionality comprising a nitro group, wherein the nitro group is a functional group. Aromatic functionalities include halogenated aromatic functionalities. Exemplary aromatic functionalities include, but are not limited to phenyl, 4-trifluoromethylphenyl, 4-chloromethylphen-1-yl, 3-trichloromethylphen-1-yl (3-$CCl_3$Ph-), 4-(3-bromoprop-1-yl)phen-1-yl (4-$BrCH_2CH_2CH_2$Ph-), 4-aminophen-1-yl (4-$H_2$NPh-), 4-hydroxymethylphen-1-yl (4-$HOCH_2$Ph-), 4-methylthiophen-1-yl (4-$CH_3$SPh-), 3-methoxyphen-1-yl and 2-nitromethylphen-1-yl (2-$NO_2CH_2$Ph), naphthyl.

As used herein the term "aliphatic functionality" refers to an organic functionality having a valence of at least one consisting of a linear or branched array of atoms that is not cyclic. As used herein, the term "aliphatic ester functionality" refers to an array of atoms having a valence of at least one comprising at least one aliphatic functionality group attached to a ester functionality, i.e., aliphatic group-OC(O)—. Aliphatic functionalities are defined to comprise at least one carbon atom. The array of atoms comprising the aliphatic functionality may include heteroatoms such as nitrogen, sulfur, silicon, selenium and oxygen or may be composed exclusively of carbon and hydrogen. For convenience, the term "aliphatic functionality" is defined herein to encompass, as part of the "linear or branched array of atoms which is not cyclic" a wide range of functional groups such as alkyl groups, haloalkyl groups, alcohol groups, ether groups, carboxylic acid groups, acyl groups (for example carboxylic acid derivatives such as esters and amides), amine groups and nitro groups. For example, the 4-methylpent-1-yl is a $C_6$ aliphatic functionality comprising a methyl group, wherein the methyl group is a functional group which is an alkyl group. Similarly, the 4-nitrobut-1-yl group is a $C_4$ aliphatic functionality comprising a nitro group, wherein the nitro group is a functional group. An aliphatic functionality may be a haloalkyl group which comprises one or more halogen atoms which may be the same or different. Halogen atoms include, for example; fluorine, chlorine, bromine, and iodine. Exemplary aliphatic functionalities include, but are not limited to methyl, ethyl, propyl, isopropyl, butyl, isobutyl, pentyl, isopentyl, trifluoromethyl, bromodifluoromethyl, chlorodifluoromethyl, chloromethyl, trichloromethyl, bromoethyl, 2-hexyl, hexamethylene, hydroxymethyl (i.e., —$CH_2OH$), mercaptomethyl (—$CH_2SH$), methylthio (—$SCH_3$), methylthiomethyl (—$CH_2SCH_3$), methoxy, methoxycarbonyl ($CH_3OCO$—), nitromethyl (—$CH_2NO_2$) and thiocarbonyl.

"BPA" is herein defined as bisphenol A and is also known as 2,2-bis(4-hydroxyphenyl)propane, 4,4'-isopropylidenediphenol and p,p-BPA.

Disclosed herein are polycyclic dihydroxy compounds having a Formula (I),

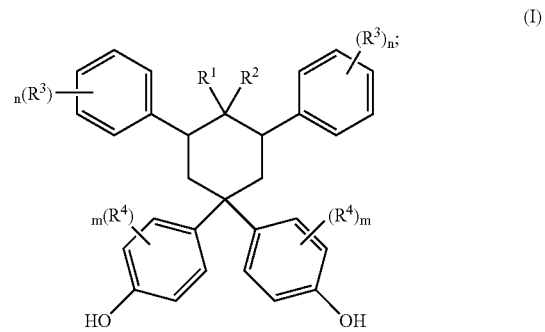

wherein $R^1$, $R^2$, $R^3$, $R^4$, "n" and "m" are defined as above.

In one embodiment the polycyclic dihydroxy compound comprises a compound of Formula (II)

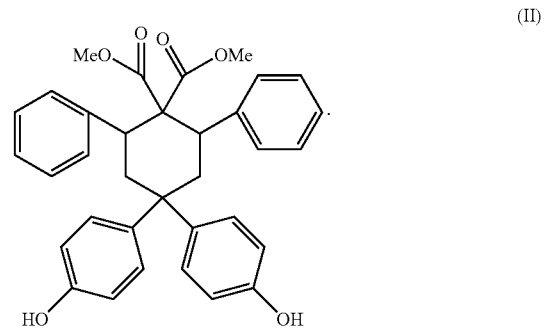

The compound of Formula (II) may hereinafter also be referred to as methyl-4,4-bis(4-hydroxyphenyl)-2,6-diphenyl cyclohexane-1,1-dicarboxylate.

The process for making the dihydroxy compound of Formula (I) comprises the following steps. The first step comprises reacting acetone with a compound of Formula (III) in the presence of a first catalyst to produce dibenzalacetone of Formula (IV)

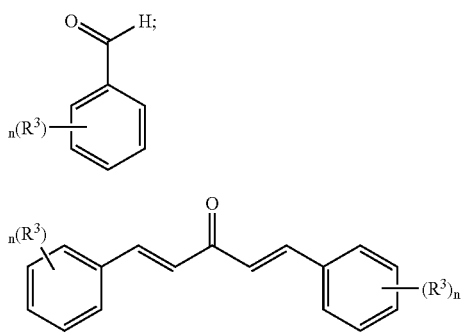

wherein $R^3$ and "n" have the same meaning as defined above.

Exemplary compounds of Formula (III) include, but are not limited to, benzaldehyde, 4-methyl benzaldehyde, 2-methyl benzaldehyde, 3-methyl benzaldehyde, 4-ethyl benzaldehyde, 2-ethyl benzaldehyde, 3-isopropyl-6-methyl benzaldehyde, 4-(N,N-dipropylamino)benzaldehyde, 4-ethoxybenzaldehyde, 4-butylbenzaldehyde, 4-tertbutyl benzaldehyde, and 4-isopropylbenzaldehyde. In one embodiment the compound of Formula (III) comprises benzaldehyde.

The amount of the compound of Formula (III) employed in the reaction can be about 2 to about 10 moles per mole of acetone employed. Within this range the amount may be greater than or equal to about 3 moles, or, more specifically, greater than or equal to about 6 moles. Also within this range the amount may be less than or equal to about 9 moles, or, more specifically less than or equal to about 7 moles.

Suitable first catalysts include but are not limited to alkali metal hydroxide and dry hydrogen chloride.

Specific examples of suitable alkali metal hydroxides that may be employed as the first catalyst in the reaction of acetone with the compound of Formula (II) include, but are not limited to sodium hydroxide, potassium hydroxide, lithium hydroxide, rubidium hydroxide cesium hydroxide or a combination of two or more of the foregoing alkali metal hydroxides. In one embodiment the alkali metal hydroxide comprises sodium hydroxide. The alkali metal hydroxides can be added as an aqueous solution or as solids. The amount of alkali metal hydroxide employed in the reaction can be about 6 moles to about 15 moles per mole of acetone employed. Within this range the amount may be greater than or equal to about 7 moles, or, more specifically greater than or equal to about 9 moles. Also within this range the amount may be less than or equal to about 13 moles, or, more specifically less than or equal to about 12 moles.

Specific examples of suitable solvents that can be employed in the reaction of acetone with a compound of Formula (III) in the presence of an alkali earth metal hydroxide to produce the dibenzalacetone of Formula (IV) include, but are not limited know ethanol, methanol, isopropanol, n-propanol, n-butanol, isobutanol or mixtures of two or more of the foregoing solvents. In one embodiment the solvent employed comprises ethanol, methanol, or a combination of ethanol and methanol. The amount of solvent employed in the reaction of acetone with a compound of Formula (III) in the presence of an alkali earth metal hydroxide to produce the dibenzalacetone of Formula (IV) can be about 2 liters to about 10 liters per mole of acetone. Within this range the amount may be greater than or equal to about 3 liters, or, more specifically, greater than or equal to about 5 liters. Also within this range the amount may be less than or equal to about 9 liters, or, more specifically less than or equal to about 7 liters.

The temperature at which the reaction of acetone with the compound of Formula (III) occurs to produce the dibenzalacetone of Formula (IV) is about 20° C. to about 40° C. Within this range the temperature may be greater than or equal to about 22° C., or, more specifically, greater than or equal to about 25° C. Also within this range the temperature may be less than or equal to about 35° C., or, more specifically, less than or equal to about 30° C. The time taken for the reaction of acetone with the compound of Formula (III) to produce the dibenzalacetone of Formula (IV) can be about 15 minutes to about 4 hours. Within this range the time may be greater than or equal to about 1 hour, or, more specifically, greater than or equal to about 1.5 hours. Also within this range the time may be less than or equal to about 3 hours, or, more specifically, less than or equal to about 2 hours.

The second step comprises reacting the dibenzalacetone of Formula (IV) in the presence of a second catalyst with a compound of Formula (V) to produce a compound of Formula (VI)

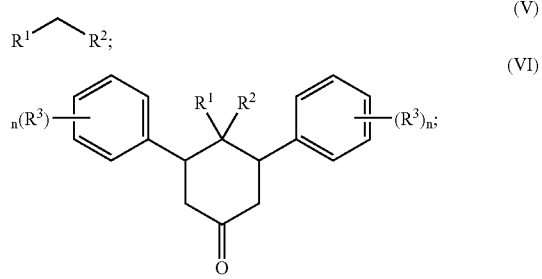

wherein $R^1$, $R^2$, $R^3$, and "n" have the same meaning as defined above.

Suitable compounds having Formula (V) include, but are not limited to dimethyl malonate, diethyl malonate, diisopropyl malonate, ethyl cyanoacetate and methyl cyanoacetate. In one embodiment the compound of Formula (V) may comprise dimethyl malonate or ethyl cyanoacetate.

The amount of the compound of Formula (V) employed in the reaction can be about 1 mole to about 6 moles per mole of dibenzalacetone compound having Formula (IV). Within this range the amount may be greater than or equal to about 2 moles, or, more specifically, greater than or equal to about 2.5 moles. Also within this range the amount may be less than or equal to about 5.5 moles, or, more specifically, less than or equal to about 5 moles.

Suitable second catalysts include, but are not limited to an alkoxide, glacial acetic acid with sulfuric acid, ammonium ylides, 1,4-diazabicyclo[2.2.2]octane, rhodium acetate, sodium carbonate or benzyltriethylammonium hydroxide (hereinafter also mentioned as Triton® B).

Specific examples of alkoxides that may be employed as second catalysts in the reaction of compound having Formula (IV) with the compound of Formula (V) include, but are not limited to aluminum isopropoxide, aluminum phenoxide, aluminum tributoxide, lithium 2-ethylhexodide, lithium ethoxide, lithium isopropoxide, lithium methoxide, magnesium ethoxide, magnesium methoxide, potassium ethoxide, potassium isobutoxide, potassium methoxide, potassium tert-butoxide, sodium benzyloxide, sodium ethoxide, sodium phenoxide, sodium tert-butoxide, sodium ter-pentoxide, sodium methanethiolate, or mixtures of two or more of the foregoing. In one embodiment the alkoxide employed is sodium methoxide.

Specific examples of suitable solvents that may be employed in the reaction of compound having Formula (IV) in the presence of alkoxide, with the compound of Formula (V) include, but are not limited to ethanol, methanol, isopropanol, n-propanol, n-butanol, isobutanol or mixtures of two or more of the foregoing. In one embodiment the solvent employed comprises ethanol, methanol, or a combination of methanol and ethanol. The amount of solvent employed in the reaction of compound having Formula (IV) in the presence of alkoxide with the compound of Formula (V) comprises about 1 liter to about 10 liters per mole of dibenzalacetone compound having Formula (IV). Within this range the amount may be greater than or equal to about 2 liters, or, more specifically, greater than or equal to about 3 liters. Also within this range the amount may be less than or equal to about 6 liters, or, more specifically, less than or equal to about 5 liters.

The temperature of the reaction of compound having Formula (IV) in the presence of alkoxide, with the compound of Formula (V) can be about 50° C. to about 80° C. Within this range the temperature may be greater than or equal to about 55° C., or, more specifically, greater than or equal to about 60° C. Also within this range the temperature may be less than or equal to about 75° C., or, more specifically, less than or equal to about 70° C. The time for the reaction of compound having Formula (IV) in the presence of alkoxide, with the compound of Formula (V) can be about 3 hours to about 24 hours. Within this range the time may be greater than or equal to about 4, or, more specifically, greater than or equal to about 6. Also within this range the time may be less than or equal to about 16 hours, or, more specifically, less than or equal to about 12 hours.

The amount of alkoxide employed in the reaction can be about 0.01 to about 0.6 mole per mole of dibenzalacetone compound of Formula (IV). Within this range the amount may be greater than or equal to about 0.02 moles, or, more specifically, greater than or equal to about 0.08 moles. Also within this range the amount may be less than or equal to about 0.5 moles, or, more specifically, less than or equal to about 0.4 moles.

The third step comprises reacting the compound of Formula (VI) with a compound of Formula (VII) in the presence of an acid catalyst and a promoter to produce the compound of Formula (I),

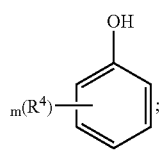

(VII)

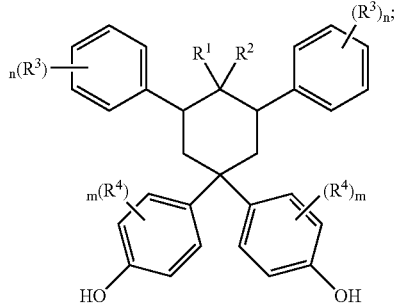

(I)

wherein $R^1$, $R^2$, $R^3$, $R^4$, "n" and "m" have the same meaning as defined above.

Specific examples of suitable compounds of Formula (VII) include, but are not limited to phenol, 2,6-dimethylphenol, 2,3,6-trimethylphenol, 2,6-di-tert-butylphenol, 2-tert-butylphenol, meta-cresol, ortho-cresol, ortho-phenylphenol, ortho-chlorophenol, ortho-benzylphenol, ortho-vinylphenol, and mixtures of two or more of the foregoing. In one embodiment, the compound of Formula (VII) comprises phenol, m-cresol, o-cresol, or a mixture of two or more of the foregoing. In another embodiment the compound of Formula (VII) is phenol.

The amount of the compound of Formula (VII) employed in the reaction can be about 5 moles to about 20 moles per mole of compound of Formula (VI). Within this range the amount may be greater than or equal to about 6 moles, or, more specifically, greater than or equal to about 8 moles. Also within this range the amount may be less than or equal to about 15 moles, or, more specifically, less than or equal to about 10 moles.

Suitable acid catalysts that may be employed in the reaction of the compound having Formula (VI) with the compound of Formula (VII) include, but are not limited to mineral acids, cation exchange resins and solid acid catalysts. Non-limiting examples of mineral acids include hydrogen chloride liquid, hydrogen chloride gas, sulfuric acid and nitric acid. As used herein the term "cation exchange resin" refers to an ion exchange resin in the hydrogen form, wherein the hydrogen ions are bound to the active sites which can be removed either by dissociation in solution or by replacement with other positive ions. The active sites of the resin have different attractive strengths for different ions, and this selective attraction serves as a means for ion exchange. Non-limiting examples of suitable cation exchange resins include the series of sulfonated divinylbenzene-crosslinked styrene copolymers, such as for example, copolymers crosslinked with about 1 to about 20 weight percent of divinylbenzene relative to the overall weight of the acidic ion exchange resin. More specifically, suitable catalysts include cation exchange resins crosslinked with greater than or equal to about 8 weight percent of divinylbenzene relative to the overall weight of the acidic ion exchange resin catalyst, such as for example, Amberlyst 15® commercially available from Aldrich Chemical Company, Bayer K2431® commercially available from Bayer Company and T-66® commercially available from Thermax, Ltd.

In one embodiment the amount of acid catalyst employed in the reaction can be about 0.5 weight percent to about 10 weight percent of an overall weight of the reaction mixture. Within this range the amount may be greater than or equal to about 1 weight percent, or, more specifically, greater than or equal to about 3 weight percent. Also within this range the amount may be less than or equal to about 8 weight percent, or, more specifically, less than or equal to about 5 weight percent. As used herein, the term "reaction mixture" refers to a mixture comprising the compounds of Formula (VI) and Formula (VII). As used herein, the term "overall weight of the reaction mixture" refers to the weight of a reaction mixture comprising the compounds of Formula (VI) and Formula (VII).

Suitable examples of promoters include, but are not limited to 3-mercaptopropionic acid (hereinafter called 3-MPA), a substituted or an unsubstituted benzyl mercaptan, 3-mercapto-1-propanol, ethyl 3-mercaptopropionate, 1,4-bis(mercaptomethyl)benzene, 2-mercaptoethane-sulfonic acid, 3-mercaptopropanesulfonic acid, 4-mercaptobutanesulfonic acid, 4-mercaptopentanesulfonic acid, 3-mercapto-2,2-dimethylpropanesulfonic acid, 2,3-dimercaptopropanesulfonic acid, mercaptopropane-2,3-disulfonic acid, 2-benzyl-4-mercaptobutanesulfonic acid, 5-mercaptopentane-sulfonic acid, methanethiol, ethanethiol, isopropanethiol, butanethiol, resorcinol, catechol, hytdroquionone, or the mono- and di-methyl or mono- and di-ethyl ethers thereof, para-ethylphenol, ortho-cresol, para-cresol, phloroglucinol, alpha-naphthol, 5-methyl-alpha-naphthol, 6-isobutyl-alpha-naphthol, 1,4-dihydroxynaphthalene, 6-hexyl-1,4-dihydroxy naphthalene and 6-methyl-4-methoxy-alpha-naphthalene. In one embodiment resorcinol or 3-mercaptopropionic acid is employed as the promoter.

In one embodiment the amount of promoter employed in the reaction is about 0.2 moles to about 0.5 moles based on the moles of the compound of Formula (VI) employed. Within this range the amount may be greater than or equal to about 0.25 moles, or, more specifically greater than or equal to about 0.3 moles. Also within this range the amount may be less than or equal to about 0.45 moles, or, more specifically, less than or equal to about 0.4 moles.

Specific examples of suitable solvents that may be employed in the reaction of compound having in the reaction of the compound having Formula (VI) with the compound of Formula (VII) include, but are not limited to toluene, petroleum ether, xylene, benzene hexane, heptane, octane, decane or a mixture of two or more of the foregoing solvents. In one embodiment the solvent employed comprises toluene or petroleum ether. In another embodiment the solvent employed comprises toluene. The amount of solvent employed in the reaction of the compound having Formula (VI) with the compound of Formula (VII) can be about 1 liter to about 10 liters per mole of Formula (VI) employed. Within this range the amount may be greater than or equal to about 2 liters, or, more specifically, greater than or equal to about 3 liters. Also within this range the amount may be less than or equal to about 6 liters, or, more specifically, less than or equal to about 5 liters. In one embodiment an excess of the compound of Formula (VII) may be employed as the solvent in the reaction.

The temperature at which the reaction of the compound having Formula (VI) with the compound of Formula (VII) can be about 40° C. to about 120° C. Within this range the temperature may be greater than or equal to about 45° C., or, more specifically, greater than or equal to about 60° C. Also within this range the temperature may be less than or equal to about 100° C., or, more specifically, less than or equal to about 80° C. The time taken for the reaction of the compound having Formula (VI) with the compound of Formula (VII) can be about 10 hours to about 16 hours. Within this range the time may be greater than or equal to about 12 hours, or, more specifically, greater than or equal to about 13 hours. Also within this range the time may be less than or equal to about 15 hours, or, more specifically, less than or equal to about 14 hours.

The product compound having Formula (I) may be isolated by using appropriate methods. For example when isolating compounds having Formula (I) the reaction mixture may be initially mixed with an organic solvent or a mixture of organic solvents such as toluene and petroleum ether and filtered. The resultant filter cake may be suspended in hot water and filtered again. In some cases the resulting solids may further be crystallized from a solvent such as isopropanol.

In one embodiment a process for producing the polycyclic dihydroxy compounds of Formula (II) comprises reacting acetone with benzaldehyde having Formula (XXIV) in presence of sodium hydroxide to produce dibenzalacetone having Formula (XXV)

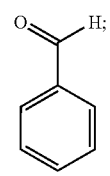
(XXIV)

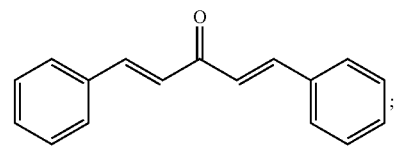
(XXV)

reacting the dibenzalacetone having Formula (XXV) in presence of sodium methoxide with dimethyl malonate having Formula (XXVI) to produce methyl-2,6-diphenyl-cyclohexane-4-one-1,1-dicarboxylate having Formula (XXVII)

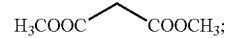
(XXVI)

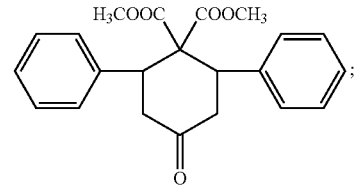
(XXVII)

reacting methyl-2,6-diphenyl-cyclohexane-4-one-1,1-dicarboxylate with phenol having Formula (XXVIII) in presence of an acid catalyst and a promoter to produce methyl-4,4'-bis(4-hydroxy-phenyl)-2,6-diphenyl-cyclohexane-1,1-dicarboxylate having Formula (II),

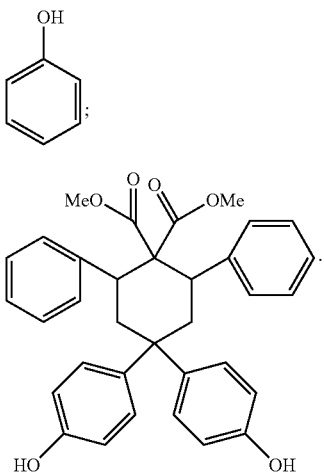

(XXVIII)

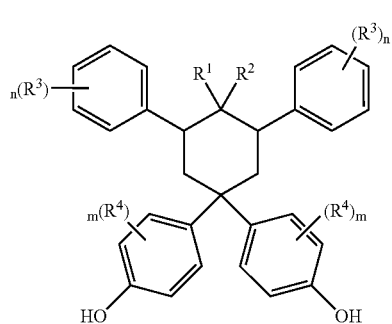

In one embodiment a composition comprises a compound of Formula (I)

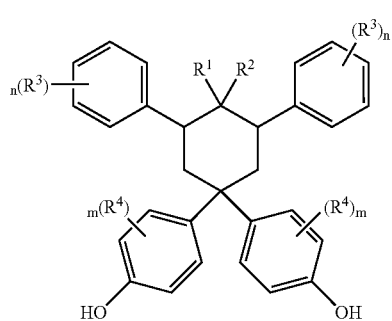

(I)

wherein $R^1$, $R^2$, $R^3$, $R^4$, "n" and "m" have the same meaning as defined above.

Disclosed herein are polymers prepared using polycyclic dihydroxy compounds. These polymers may find use in high heat and optical applications.

In one embodiment a polymer comprises structural units derived from a polycyclic dihydroxy compound of Formula (I)

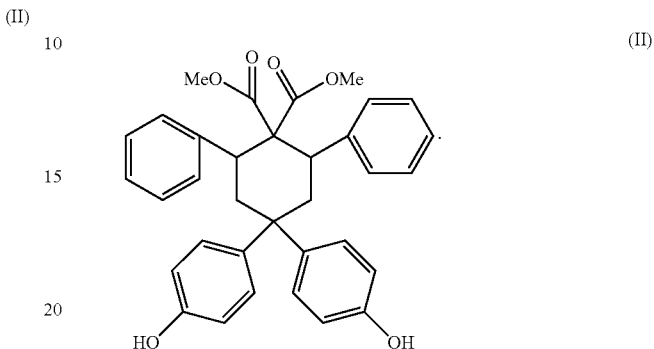

wherein $R^1$, $R^2$, $R^3$, $R^4$, "n" and "m" have the same meaning as defined above. A variety of polymers may comprise the structural units derived from the polycyclic dihydroxy compound of Formula (I), including, but not limited to, polycarbonate, polyester, copolyester-polycarbonate, polyurethane, and epoxide containing polymers.

In one embodiment the polymer comprises structural units derived from a polycyclic dihydroxy compound of Formula (II)

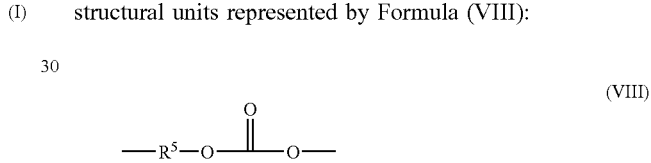

The compound of Formula (II) may also be referred to as methyl-4,4-bis(4-hydroxyphenyl)-2,6-diphenyl cyclohexane-1,1-dicarboxylate.

"Polycarbonates" as used herein are polymers comprising structural units represented by Formula (VIII):

wherein at least about 60 percent of the total number of $R^5$ groups are aromatic functionalities and the balance thereof are aliphatic, alicyclic, or aromatic functionalities and further wherein at least two $R^5$ groups are derived from a polycyclic dihydroxy compound of Formula (I).

The aromatic functionality may also comprise a functionality of the Formula (IX):

$$-A^1-Y^1-A^2-$$ (IX)

wherein each of $A^1$ and $A^2$ is a monocyclic divalent aromatic functionality and $Y^1$ is a bridging functionality having one or two atoms that separate $A^1$ from $A^2$. In an exemplary embodiment, one atom separates $A^1$ from $A^2$. Illustrative non-limiting examples of functionalities of this type are —O—, —S—, —S(O)—, —S(O$_2$)—, —C(O)—, methylene, cyclohexyl-methylene, 2-[2.2.1]-bicycloheptylidene, ethylidene, isopropylidene, neopentylidene, cyclohexylidene, cyclopentadecylidene, cyclododecylidene, and adamantylidene. The bridging functionality $Y^1$ may be a hydrocarbon group or a saturated hydrocarbon group such as methylene, cyclohexylidene, or isopropylidene.

"Polyesters" as used herein may comprise repeating structural units of the Formula (X)

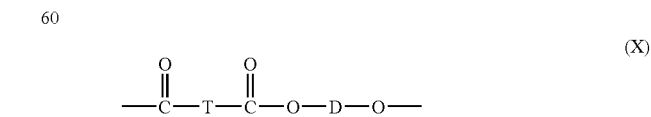

wherein D is derived from a divalent functionality derived from a dihydroxy compound, and may be, for example, a cycloaliphatic functionality having 6 to 10 carbon atoms, an aromatic functionality having 6 to 20 carbon atoms or an aliphatic functionality having 2 to 10 carbon atoms and wherein at least two of D are derived from a polycyclic dihydroxy compound of Formula (I); and T is a divalent functionality derived from a dicarboxylic acid, and may be, for example, a cycloaliphatic functionality having 6 to 10 carbon atoms, an aromatic functionality having 6 to 20 carbon atoms or an aliphatic functionality having 2 to 10 carbon atoms.

In one embodiment, D comprises an aliphatic functionality having 2 to 10 carbon atoms. In another embodiment, D may be derived from an aromatic dihydroxy compound of Formula (XI):

(XI)

wherein each $R^f$ is independently a halogen atom, an aliphatic functionality having 1 to 10 carbon atoms and n is an integer having a value 0 to 4. Examples of compounds that may be represented by the Formula (XI) include, but are not limited to resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resoreinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like; or combinations comprising at least one of the foregoing compounds.

In one embodiment the T is a divalent functionality derived from a dicarboxylic acid compound of Formula (XVII)

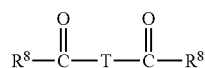

(XVII)

wherein $R^8$ is independently at each occurrence hydroxy, chloro, or $OR^9$, wherein $R^9$ is independently at each occurrence selected from the group consisting of an aliphatic functionality having 1 to 10 carbons, a cycloaliphatic functionality having 3 to 10 carbons, and an aromatic functionality having 6 to 10 carbons. In one embodiment the divalent functionality "T" comprises a cycloaliphatic functionality having 6 to 10 carbon atoms, an aromatic functionality having 6 to 20 carbon atoms, or an aliphatic functionality having 2 to 10 carbon atoms.

Examples of aromatic dicarboxylic acids that may be used to prepare the polyesters include, but are not limited to 1,6-hexanedioic acid, phthalic acid, isophthalic acid, terephthalic acid, fumaric acid, maleic acid, azelaic acid, glutaric acid, adipic acid, suberic acid, sebacic acid, malonic acid, succinic acid, 1,2-di(p-carboxyphenyl)ethane, 4,4'-dicarboxydiphenyl ether, 4,4'-bisbenzoic acid, and mixtures comprising at least one of the foregoing acids. Acids containing fused rings can also be present, such as in 1,4-, 1,5-, or 2,6-naphthalenedicarboxylic acids. Specific dicarboxylic acids are terephthalic acid, isophthalic acid, naphthalene dicarboxylic acid, cyclohexane dicarboxylic acid, or mixtures thereof. A specific dicarboxylic acid comprises a mixture of isophthalic acid and terephthalic acid wherein the weight ratio of terephthalic acid to isophthalic acid is about 10:1 to about 0.2:9.8. In another specific embodiment, D is a $C_{2-6}$ alkylene functionality and T is p-phenylene, m-phenylene, naphthalene, a divalent cycloaliphatic functionality, or a mixture thereof. This class of polyester includes the poly(alkylene terephthalates).

"Copolyester-polycarbonate" or "copolyestercarbonate" or "polyester carbonate" as used herein are copolymers containing recurring carbonate units of Formula (VIII) in addition to the repeating units of Formula (X) as defined above. In one embodiment either repeating carbonate units of Formula (VIII) or repeating units of Formula (X) or repeating units of Formula (VIII) and repeating units of Formula (X) comprise structural units derived from the polycyclic dihydroxy compound of Formula (I).

Polyurethane as used herein are polymers containing recurring units having Formula (XII)

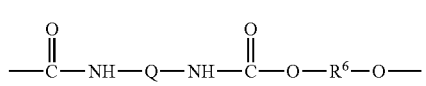

(XII)

wherein O—$R^6$—O is a divalent functionality derived from a dihydroxy compound or polyhydroxy compound; wherein at least two of $R^6$ are each independently structural units derived from a dihydroxy compound of Formula (I); and wherein "Q" is a divalent functionality derived from a diisocyanate compound, having Formula (XIII)

$$Q(NCO)_2 \qquad (XIII)$$

wherein Q comprises a divalent aliphatic functionality having 2 to 28 carbons, a divalent cycloaliphatic functionality having 4 to 15 carbons, or a divalent aromatic functionality having 6 to 15 carbons.

Suitable examples of diisocyanate include but are not limited to, toluene-2,6-diisocyanate, 1,6-hexamethylene diisocyanate, 4,4'-diphenyl methane diisocyanate, 2,4'-diphenyl methane diisocyanate, 1,3-phenylene diisocyanate, 1,4-phenylene diisocyanate, toluene-2,4-diisocyanate, and combinations of two or more of the foregoing diisocyanate compounds.

Epoxide-containing polymer as used herein are polymers having the structure of Formula (XIV)

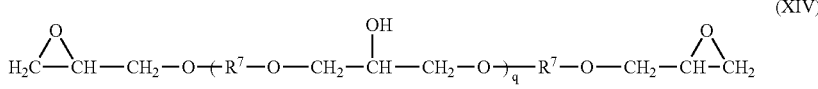

(XIV)

wherein $R^7$ is a divalent functionality derived from a dihydroxy compound; wherein at least two of $R^7$ are each structural units derived from a dihydroxy compound of Formula (I); and wherein "q" is 2 to about 20.

In one embodiment a polycarbonate comprises at least two structural units derived from a dihydroxy compound of Formula (II)

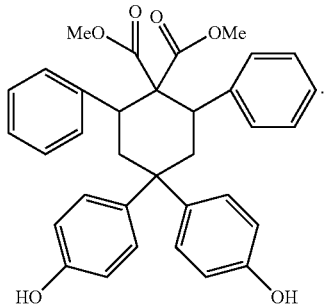

(II)

The polymer described above may be a homopolymer containing structural units derived from a single polycyclic dihydroxy compound represented by Formula (I) or a copolymer comprising structural units derived from two or more of the polycyclic dihydroxy compounds represented by Formula (I) or may be a copolymer comprising structural units derived from one or more polycyclic dihydroxy compound represented by Formula (I) and structural units derived from other dihydroxy compounds. Accordingly, in one embodiment the polymer may comprise 1 mole percent to about 100 mole percent of $R^5$ units derived from a polycyclic dihydroxy compound of Formula (I). Within this range the amount may be greater than or equal to about 5 mole percent, or, more specifically, greater than or equal to about 10 mole percent. Also within this range the amount may be less than or equal to about 80 mole percent, or, more specifically less than or equal to about 50 mole percent.

In one embodiment the dihydroxy compounds that may be useful in forming the copolymer with the polycyclic dihydroxy compound of Formula (I) may be represented by Formula (XVIII)

HO—$R^{10}$—OH  (XVIII)

wherein $R^{10}$ includes a functionality of Formula (IX),

-$A^1$-$Y^1$-$A^2$-;  (IX)

and wherein $Y^1$, $A^1$ and $A^2$ are as defined above. In another embodiment the dihydroxy compound includes bisphenol compounds of general Formula (XIX):

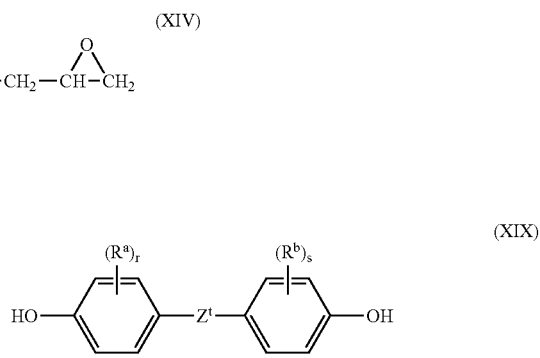

(XIX)

wherein $R^a$ and $R^b$ each represent a halogen atom or an aliphatic functionality having $C_1$-$C_{10}$ carbon atoms and may be the same or different; r and s are each independently integers of 0 to 4; and $Z^t$ represents one of the groups of Formula (XX):

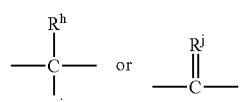

(XX)

wherein $R^h$ and $R^i$ each independently represent a hydrogen atom or an aliphatic functionality having $C_1$-$C_{10}$ carbon atoms or a cycloaliphatic functionality having $C_3$-$C_{10}$ carbon atoms and $R^j$ is a divalent aliphatic functionality having $C_1$-$C_{10}$ carbon atoms.

Some illustrative, non-limiting examples of suitable dihydroxy compounds that may be used in combination with the polycyclic dihydroxy compound of Formula (I) include, but are not limited to the following: resorcinol, 4-bromoresorcinol, hydroquinone, methyl hydroquinone, 1,1-bis-(4-hydroxy-3-methylphenyl)cyclohexane, 2-phenyl-3,3-bis(4-hydroxyphenyl)phthalimidine, eugenol siloxane bisphenol, 4,4'-dihydroxybiphenyl, 1,6-dihydroxynaphthalene, 2,6-dihydroxynaphthalene, bis(4-hydroxyphenyl)methane, bis(4-hydroxyphenyl)diphenylmethane, bis(4-hydroxyphenyl)-1-naphthylmethane, 1,2-bis(4-hydroxyphenyl)ethane, 1,1-bis(4-hydroxyphenyl)-1-phenylethane, 2-(4-hydroxyphenyl)-2-(3-hydroxyphenyl)propane, bis(4-hydroxyphenyl)phenylmethane, 2,2-bis(4-hydroxy-3-bromophenyl)propane, 1,1-bis(hydroxyphenyl)cyclopentane, 1,1-bis(4-hydroxyphenyl)cyclohexane, 1,1-bis(4-hydroxyphenyl)isobutene, 1,1-bis(4-hydroxyphenyl)cyclododecane, trans-2,3-bis(4-hydroxyphenyl)-2-butene, 2,2-bis(4-hydroxyphenyl)adamantine, (alpha,alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, as well as combinations comprising at least one of the foregoing dihydroxy compounds.

Specific examples of the types of bisphenol compounds may include, but are not limited to 1,1-bis(4-hydroxyphenyl) methane, 1,1-bis(4-hydroxyphenyl)ethane, 2,2-bis(4-hydroxyphenyl)propane (hereinafter "bisphenol A" or "BPA"), 2,2-bis(4-hydroxyphenyl)butane, 2,2-bis(4-hydroxyphenyl) octane, 1,1-bis(4-hydroxyphenyl)propane 1,1-bis(4-hydroxyphenyl)n-butane, 2,2-bis(4-hydroxy-1-methylphenyl)propane, and 1,1-bis(4-hydroxy-t-butylphenyl)propane. Combinations comprising at least one of the foregoing dihydroxy compounds may also be used. In one embodiment the bisphenol compound employed is bisphenol A.

The polymer may be a branched polymer. Branched polymers comprising structural units derived from the dihydroxy compound of Formula (I) may be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include, but are not limited to trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol-PA (4(4(1,1-bis(p-hydroxyphenyl)-ethyl)alpha,alpha-dimethyl benzyl)phenol), 4-chloroformyl phthalic anhydride, trimesic acid, and benzophenone tetracarboxylic acid. All types of polycarbonate end groups are contemplated as being useful in the polycarbonate composition, provided that such end groups do not significantly affect desired properties of the thermoplastic compositions.

In one specific embodiment, the polymer is a polycarbonate wherein the polycarbonate is a linear homopolymer derived from polycyclic dihydroxy compounds of Formula (I) or a copolymer comprising repeating units derived from polycyclic dihydroxy compounds of Formula (I) and repeating units derived from bisphenol A. In one embodiment the polycarbonate may have a refractive index of greater than or equal to 1.500. In another embodiment the polycarbonate may have a refractive index of greater than or equal to 1.580. In yet another embodiment the polycarbonate may have a refractive indeed of greater that or equal to 1.600. In one embodiment the polycarbonate may have a Tg greater than or equal to 150° C. In another embodiment the polycarbonate may have a Tg greater than or equal to 180° C. In yet another embodiment the polycarbonate may have a Tg greater than or equal to 200° C. The polycarbonates may have a weight average molecular weight of about 10,000 to about 200,000, specifically about 20,000 to about 100,000 as measured by gel permeation chromatography.

Suitable polycarbonates, polyesters and copolyester-carbonates may be manufactured by processes such as interfacial polymerization and melt polymerization. Although the reaction conditions for interfacial polymerization may vary, an exemplary process generally involves dissolving or dispersing a dihydric phenol reactant in aqueous sodium hydroxide or potassium hydroxide, adding the resulting mixture to a suitable water-immiscible solvent medium, and contacting the reactants with a carbonate precursor in the presence of a suitable catalyst such as triethylamine or a phase transfer catalyst, under controlled pH conditions, for example, about 8 to about 10. The most commonly used water immiscible solvents include, but are not limited to methylene chloride, 1,2-dichloroethane, chlorobenzene and toluene. Suitable carbonate precursors include, for example, a carbonyl halide such as carbonyl bromide or carbonyl chloride, or a haloformate such as a bishaloformate of a dihydric phenol (for example, the bischloroformates of bisphenol A, hydroquinone, or the like) or a glycol (for example, the bishaloformate of ethylene glycol, neopentyl glycol, polyethylene glycol, or the like) or esters (for example, bismethylsalicylate (bMSC)) or diphenyl carbonate (DPC). Combinations comprising at least one of the foregoing types of carbonate precursors may also be used. The resultant polymers, may have a weight average molecular weight (Mw) of 10,000 to about 200,000, or, more specifically about 20,000 to about 100,000 as measured by gel permeation chromatography.

A chain stopper (also referred to as a capping agent) may be included during polymerization. The chain-stopper limits molecular weight growth rate, and so controls molecular weight in the polycarbonate. A chain-stopper may be at least one of mono-phenolic compounds, mono-carboxylic acid chlorides, and mono-chloroformates.

For example, mono-phenolic compounds suitable as chain stoppers include monocyclic phenols, such as phenol, $C_1$-$C_{22}$ alkyl-substituted phenols, p-cumyl-phenol, p-tertiary-butyl phenol, hydroxy diphenyl; and monoethers of diphenols, such as p-methoxyphenol. Alkyl-substituted phenols include those with branched chain alkyl substituents having 8 to 9 carbon atoms. A mono-phenolic UV absorber may be used as capping agent. Such compounds include 4-substituted-2-hydroxybenzophenones and their derivatives, aryl salicylates, monoesters of diphenols such as resorcinol monobenzoate, 2-(2-hydroxyaryl)-benzotriazoles and their derivatives, 2-(2-hydroxyaryl)-1,3,5-triazines and their derivatives. Specifically, mono-phenolic chain-stoppers include phenol, p-cumylphenyl, and resorcinol monobenzoate.

Mono-carboxylic acid chlorides may also be suitable as chain stoppers. These include monocyclic, mono-carboxylic acid chlorides such as benzoyl chloride, $C_1$-$C_{22}$ alkyl-substituted benzoyl chloride, toluoyl chloride, halogen-substituted benzoyl chloride, bromobenzoyl chloride, cinnamoyl chloride, 4-nadimidobenzoyl chloride, and mixtures thereof; polycyclic, mono-carboxylic acid chlorides such as trimellitic anhydride chloride, and naphthoyl chloride; and mixtures of monocyclic and polycyclic mono-carboxylic acid chlorides. Chlorides of aliphatic monocarboxylic acids with up to 22 carbon atoms are suitable. Functionalized chlorides of aliphatic monocarboxylic acids, such as acryloyl chloride and methacryloyl chloride, are also suitable. Also suitable are mono-chloroformates including monocyclic, mono-chloroformates, such as phenyl chloroformate, alkyl-substituted phenyl chloroformate, p-cumyl phenyl chloroformate, toluene chloroformate, and mixtures thereof.

Among the phase transfer catalysts that may be used are catalysts of the Formula $(R^g)_4Y^+X$, wherein each $R^g$ is the same or different, and is an alkyl group having 1 to 10 carbon atoms; Y is a nitrogen or phosphorus atom; and X is a halogen atom or an aliphatic functionality having 1 to 8 carbon atoms or aromatic functionality having 6 to 188 carbon atoms. Suitable phase transfer catalysts include, for example, [CH₃(CH₂)₃]₄NX, [CH₃(CH₂)₃]₄PX, [CH₃(CH₂)₅]₄NX, [CH₃(CH₂)₆]₄NX, [CH₃(CH₂)₄]₄NX, CH₃[CH₃(CH₂)₃]₃NX, and CH₃[CH₃(CH₂)₂]₃NX, wherein X is chloride, bromide, an aliphatic functionality having 1 to 8 carbon atoms or aromatic functionality having 6 to 188 carbon atoms. An effective amount of a phase transfer catalyst may be about 0.1 to about 10 wt. percent based on the weight of bisphenol in the phosgenation mixture. In another embodiment an effective amount of phase transfer catalyst may be about 0.5 to about 2 wt. percent based on the weight of bisphenol in the phosgenation mixture.

Alternatively, melt processes may be used to make the polycarbonates. Generally, in the melt polymerization process, polycarbonates may be prepared by co-reacting, in a molten state, the dihydroxy reactant(s) and a diaryl carbonate ester, such as diphenyl carbonate, bis methyl salicylate or a combination thereof, in the presence of a transesterification catalyst in a Banbury® mixer, twin screw extruder, or the like to form a uniform dispersion. Volatile monohydric phenol is removed from the molten reactants by distillation and the polymer is isolated as a molten residue.

The transesterification catalysts capable of effecting reaction between the ester and the polycyclic dihydroxy compound may comprise a single compound or a mixture of compounds and may be employed in combination with one or more co-catalysts such as quaternary ammonium salts or quaternary phosphonium salts. Suitable transesterification catalysts include, but are not limited to, alkali metal hydroxides, for example, lithium hydroxide, sodium hydroxide, potassium hydroxide, and mixtures thereof; alkaline earth metal hydroxides, for example, calcium hydroxide, barium hydroxide, and mixtures thereof; alkali metal salts of carboxylic acids, for example, lithium acetate, sodium benzoate, and dipotassium dodecanedioate; alkaline earth metal salts of carboxylic acids, for example, calcium benzoate, calcium adipate, and barium acetate; salts of a polycarboxylic acid, for example, tetrasodium ethylenediamine tetracarboxylate and disodium magnesium ethylenediamine tetracarboxylate and salts of non-volatile acids, for example, alkaline earth metal salts of phosphates, alkali metal salts of phosphates, alkaline earth metal salts of phosphates, alkali metal salts of sulfates, alkaline earth metal salts of sulfates, alkali metal salts of metal oxo acids, and alkaline earth metal salts of metal oxo acids. Specific examples of salts of non-volatile acids include $NaH_2PO_3$, $NaH_2PO_4$, $Na_2H_2PO_3$, $KH_2PO_4$, $CsH_2PO_4$, $CsH_2PO_4$, $Cs_2H_2PO_4$, $Na_2SO_4$, $NaHSO_4$, $NaSbO_3$, $LiSbO_3$, $KSbO_3$, $Mg(SbO_3)_2$, $Na_2GeO_3$, $K_2GeO_3$, $Li_2GeO_3$, $MgGeO_3$, $Mg_2GeO_4$, and mixtures thereof. As used herein the term "non-volatile acid" means that the acid from which the catalyst is made has no appreciable vapor pressure under melt polymerization conditions. Examples of non-volatile acids include phosphorous acid, phosphoric acid, sulfuric acids and metal "oxo acids" such as the oxo acids of germanium, antimony, niobium and the like.

As mentioned, melt polymerization may be practiced using a co-catalyst. Typically, the co-catalyst is a quaternary ammonium salt or quaternary phosphonium salt and is used in an amount corresponding to about 10 to about 250 times the molar amount of melt polymerization catalyst used. The catalyst and co-catalyst, may be added to the reaction mixture either simultaneously, or the catalyst and co-catalyst may be added separately at different stages of the polymerization reaction.

When activated carbonate precursors (i.e., carbonate precursors that react faster than diphenyl carbonate) such as bMSC are used to make the polycarbonate, polyester and copolyestercarbonate polymers described herein the polymers can comprise certain physical differences compared to similar polymers prepared using other melt or interfacial methods. For example, such polymers typically contain some type of internal methyl salicylate "kink" structures such as shown below, and a certain amount of endcap structures indicative of the use of bMSC as shown in units represented by Formula (XXI), Formula (XXII) and Formula (XXIII)

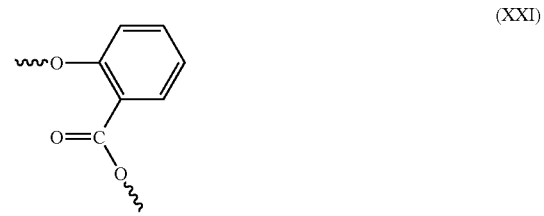

(XXI)

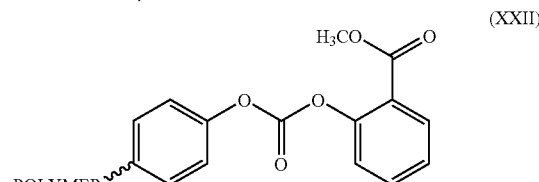

(XXII)

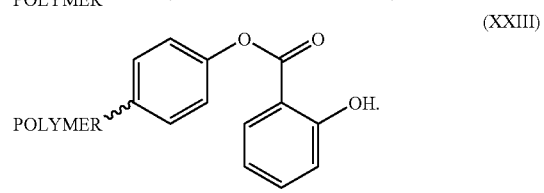

(XXIII)

The copolyester-polycarbonates may also be prepared by interfacial polymerization. Rather than utilizing the dicarboxylic acid per se, it is possible to employ the reactive derivatives of the acid, such as the corresponding acid halides, in particular the acid dichlorides and the acid dibromides. Thus, for example instead of using isophthalic acid, terephthalic acid, or mixtures thereof, it is possible to employ isophthaloyl dichloride, terephthaloyl dichloride, and mixtures thereof.

The polyurethanes may be prepared by reacting a dihydroxy compound of Formula (I) with a diisocyanate compound having Formula (XIII)

$Q(NCO)_2$ (XIII)

wherein Q comprises a divalent aliphatic radical having 2 to 28 carbons, a divalent cycloaliphatic radical having 4 to 15 carbons, or a divalent aromatic radical having 6 to 15 carbons. This reaction may be carried out in the presence of a catalyst such as diazobicyclo[2.2.2]octane (DABCO) as is known in the art.

The epoxide containing polymers can be prepared by reacting a dihydroxy compound of Formula (I) with epichlorohydrin in the presence of a base to form a diglycidyl ether and polymerizing the diglycidyl ether compound to provide the epoxide-containing polymer having Formula (XIV). This reaction can be carried out by methods known in the art.

In addition to the polymers described above, it is also possible to use combinations of the polymer with other thermoplastic polymers, for example combinations of polycarbonates and/or polycarbonate copolymers with polyamides, polyesters, other polycarbonates; copolyester-polycarbonates, olefin polymers such as ABS, polystyrene, polyethylene; polysiloxanes, polysilanes and polysulfones. As used herein, a "combination" is inclusive of all mixtures, blends and alloys. In certain embodiments the one or more additional polymers may be present in an amount less than or equal to 40 weight percent, or, more specifically, less than or equal to 35 weight percent, or, even more specifically, less than or equal to about 30 weight percent based on the total weight of the polymer composition.

In addition to the polycarbonate, the thermoplastic composition may include various additives ordinarily incorporated in thermoplastic compositions of this type, with the proviso that the additives are preferably selected so as to not significantly adversely affect the desired properties of the thermoplastic composition. Mixtures of additives may be used. Such additives may be mixed at a suitable time during the mixing of the components for forming the composition.

Exemplary additives include such materials as fillers or reinforcing agents, thermal stabilizers, radiation stabilizers, antioxidants, light stabilizers, UV stabilizers, plasticizers, visual effect enhancers, extenders, antistatic agents, catalyst quenchers, mold release agents, flame retardants, infrared shielding agents, whitening agents, blowing agents, anti-drip agents, impact modifiers and processing aids. The different additives that can be incorporated in the polymer compositions are typically commonly used and known to those skilled in the art.

Suitable fillers or reinforcing agents include, for example, silicates and silica powders such as aluminum silicate (mullite), synthetic calcium silicate, zirconium silicate, fused silica, crystalline silica graphite, natural silica sand, or the like; boron powders such as boron-nitride powder, boron-silicate powders, or the like; oxides such as TiO2, aluminum oxide, magnesium oxide, or the like; calcium sulfate (as its anhydride, dihydrate or trihydrate); calcium carbonates such as chalk, limestone, marble, synthetic precipitated calcium carbonates, or the like; talc, including fibrous, modular, needle shaped, lamellar talc, or the like; wollastonite; surface-treated wollastonite; glass spheres such as hollow and solid glass spheres, silicate spheres, cenospheres, aluminosilicate (armospheres), or the like; kaolin, including hard kaolin, soft kaolin, calcined kaolin, kaolin comprising various coatings known in the art to facilitate compatibility with the polymeric matrix, or the like; single crystal fibers or "whiskers" such as silicon carbide, alumina, boron carbide, iron, nickel, copper, or the like; fibers (including continuous and chopped fibers) such as asbestos, carbon fibers, glass fibers, such as E, A, C, ECR, R, S, D, or NE glasses, or the like; sulfides such as molybdenum sulfide, zinc sulfide or the like; barium compounds such as barium titanate, barium ferrite, barium sulfate, heavy spar, or the like; metals and metal oxides such as particulate or fibrous aluminum, bronze, zinc, copper and nickel or the like; flaked fillers such as glass flakes, flaked silicon carbide, aluminum diboride, aluminum flakes, steel flakes or the like; fibrous fillers, for example short inorganic fibers such as those derived from blends comprising at least one of aluminum silicates, aluminum oxides, magnesium oxides, and calcium sulfate hemihydrate or the like; natural fillers and reinforcements, such as wood flour obtained by pulverizing wood, fibrous products such as cellulose, cotton, sisal, jute, starch, cork flour, lignin, ground nut shells, corn, rice grain husks or the like; organic fillers such as polytetrafluoroethylene; reinforcing organic fibrous fillers formed from organic polymers capable of forming fibers such as poly(ether ketone), polyimide, polybenzoxazole, poly(phenylene sulfide), polyesters, polyethylene, aromatic polyamides, aromatic polyimides, polyetherimides, polytetrafluoroethylene, acrylic polymers, poly(vinyl alcohol) or the like; as well as additional fillers and reinforcing agents such as mica, clay, feldspar, flue dust, fillite, quartz, quartzite, perlite, tripoli, diatomaceous earth, carbon black, or the like, or combinations comprising at least one of the foregoing fillers or reinforcing agents.

The fillers and reinforcing agents may be coated with a layer of metallic material to facilitate conductivity, or surface treated with silanes to improve adhesion and dispersion with the polymeric matrix. In addition, the reinforcing fillers may be provided in the form of monofilament or multifilament fibers and may be used either alone or in combination with other types of fiber, through, for example, co-weaving or core/sheath, side-by-side, orange-type or matrix and fibril constructions, or by other methods known to one skilled in the art of fiber manufacture. Suitable cowoven structures include, for example, glass fiber-carbon fiber, carbon fiber-aromatic polyimide (aramid) fiber, and aromatic polyimide fiberglass fiber or the like. Fibrous fillers may be supplied in the form of, for example, rovings, woven fibrous reinforcements, such as 0-90 degree fabrics or the like; non-woven fibrous reinforcements such as continuous strand mat, chopped strand mat, tissues, papers and felts or the like; or three-dimensional reinforcements such as braids.

Suitable thermal stabilizer additives include, for example, organophosphites such as triphenyl phosphite, tris-(2,6-dimethylphenyl)phosphite, tris-(mixed mono- and di-nonylphenyl)phosphite or the like; phosphonates such as dimethylbenzene phosphonate or the like, phosphates such as trimethyl phosphate, or the like, or combinations comprising at least one of the foregoing heat stabilizers.

Non-limiting examples of antioxidants that can be used include tris(2,4-di-tert-butylphenyl)phosphite; 3,9-di(2,4-di-tert-butylphenoxy)-2,4,8,10-tetraoxa-3,9-diphosphaspiro[5.5]undecane; 3,9-di(2,4-dicumylphenoxy)-2,4,8,10-tetraoxa-3,9-diphosphaspiro[5.5]undecane; tris(p-nonylphenyl)phosphite; 2,2',2"-nitrilo[triethyl-tris[3,3',5,5'-tetra-tertbutyl-1,1'-biphenyl-2'-diyl]phosphite]; 3,9-distearyloxy-2,4,8,10-tetraoxa-3,9-diphosphaspiro[5.5]undecane; dilauryl phosphite; 3,9-di[2,6-di-tert-butyl-4-methylphenoxy]-2,4,8,10-tetraoxa-3,9-diphosphaspiro[5,5]undecane; tetrakis(2,4-di-tert-butylphenyl)-4,4'-bis(diphenylene)phosphonite; distearyl pentaerythritol diphosphite; diisodecyl pentaerythritol diphosphite; 2,4,6-tri-tert-butylphenyl-2-butyl-2-ethyl-1,3-propanediol phosphite; tristearyl sorbitol triphosphite; tetrakis(2,4-di-tert-butylphenyl)-4,4'-biphenylene diphosphonite; (2,4,6-tri-tert-butylphenyl)-2-butyl-2-ethyl-1,3-propanediolphosphite; triisodecylphosphite; and mixtures of phosphites containing at least one of the foregoing.

Non-limiting examples of UV stabilizers that can be used include 2-(2'-Hydroxyphenyl)-benzotriazoles, for example, the 5'-methyl-; 3',5'-di-tert.-butyl-; 5'-tert.-butyl-; 5'-(1,1,3,3-tetramethylbutyl)-; 5-chloro-3',5'-di-tert.-butyl-; 5-chloro-3'-tert.-butyl-5'-methyl-; 3'-sec.-butyl-5'-tert.-butyl-; 3'-alpha-methylbenzyl-5'-methyl; 3'-alpha-methylbenzyl-5'-methyl-5-chloro-; 4'-hydroxy-; 4'-methoxy-; 4'-octoxy-; 3',5'-di-tert.-amyl-; 3'-methyl-5'-carbomethoxyethyl-; 5-chloro-3',5'-di-tert.-amyl-derivatives and Tinuvin® 234 (available from Ciba Specialty Chemicals). Also suitable are the 2,4-bis-(2'-hydroxyphenyl)-6-alkyl-s-triazines, for example, the 6-ethyl-; 6-heptadecyl- or 6-undecyl-derivatives. 2-Hydroxybenzophenones for example, the 4-hydroxy-; 4-methoxy-; 4-octoxy-; 4-decyloxy-; 4-dodecyloxy-; 4-benzyloxy-; 4,2',4'-trihydroxy-; 2,2',4,4'-tetrahydroxy- or 2'-hydroxy-4,4'-dimethoxy-derivative. 1,3-bis-(2'-Hydroxybenzoyl)-benzenes, for example, 1,3-bis-(2'-hydroxy-4'-hexyloxy-benzoyl)-benzene; 1,3-bis-(2'-hydroxy-4'-octyloxy-benzoyl)-benzene or 1,3-bis-(2'-hydroxy-4'-dodecyloxybenzoyl)-benzene may also be employed. Esters of optionally substituted benzoic acids, for example, phenylsalicylate; octylphenylsalicylate; dibenzoylresorcin; bis-(4-tert.-butylbenzoyl)-resorcin; benzoylresorcin; 3,5-di-tert.-butyl-4-hydroxybenzoic acid-2,4-di-tert.-butylphenyl ester or -octadecyl ester or -2-methyl-4,6-di-tert.-butyl ester may likewise be employed. Acrylates, for example, alpha-cyano-beta, beta-diphenylaerylic acid-ethyl ester or isooctyl ester, alpha-carbomethoxy-cinnamic acid methyl ester, alpha-cyano-beta-methyl-p-methoxy-cinnamic acid methyl ester or -butyl ester or N(beta-carbomethoxyvinyl)-2-methyl-indoline may likewise be employed. Oxalic acid diamides, for example, 4,4'-di-octyloxy-oxanilide; 2,2'-di-octyloxy-5,5'-di-tert.-butyl-oxanilide; 2,2'-di-dodecyloxy-5,5-di-tert.-butyl-oxanilide; 2-ethoxy-2'-ethyl-oxanilide; N,N'-bis-(3-dimethyl-aminopropyl)-oxalamide; 2-ethoxy-5-tert.-butyl-2'-ethyloxanilide and the mixture thereof with 2-ethoxy-2'-ethyl-5,4'-di-tert.-butyl-oxanilide; or mixtures of ortho- and para-methoxy- as well as of o- and p-ethoxy-disubstituted oxanilides are also suitable as UV stabilizers. In one embodiment the ultraviolet light absorber used in the instant compositions is 2-(2-hydroxy-5-methylphenyl)-2H-benzotriazole; 2-(2-hydroxy-3,5-di-tert-amylphenyl)-2H-benzotriazole; 2-[2-hydroxy-3,5-di-(alpha, alpha-dimethylbenzyl)phenyl]-2H-benzotriazole; 2-(2-hydroxy-5-tert-octylphenyl)-2H-benzotriazole; 2-hydroxy-4-octyloxybenzophenone; nickel bis(O-ethyl 3,5-di-tert-butyl-4-hydroxybenzylphosphonate); 2,4-dihydroxybenzophenone; 2-(2-hydroxy-3-tert-butyl-5-methylphenyl)-2H-benzotriazole; nickel butylamine complex with 2,2'-thiobis(4-tert-butylphenol); 2-ethoxy-2'-ethyloxanilide; 2-ethoxy-2'-ethyl-5,5'-ditert-butyloxanilide or a mixture thereof.

Plasticizers, lubricants, and/or mold release agents additives may also be used. There is considerable overlap among these types of materials, which include, for example, phthalic acid esters such as dioctyl-4,5-epoxy-hexahydrophthalate; tris-(octoxycarbonylethyl)isocyanurate; tristearin; di- or polyfunctional aromatic phosphates such as resorcinol tetraphenyl diphosphate (RDP), the bis(diphenyl)phosphate of hydroquinone and the bis(diphenyl)phosphate of bisphenol-A; poly-alpha-olefins; epoxidized soybean oil; silicones, including silicone oils; esters, for example, fatty acid esters such as alkyl stearyl esters, for example, methyl stearate; stearyl stearate and pentaerythritol tetrastearate. mixtures of methyl stearate and hydrophilic and hydrophobic nonionic surfactants comprising polyethylene glycol polymers, polypropylene glycol polymers, and copolymers thereof, for example, methyl stearate and polyethylene-polypropylene glycol copolymers in a suitable solvent; waxes such as beeswax, montan wax, paraffin wax or the like.

Visual effect enhancers, sometimes known as visual effects additives or pigments may be present in an encapsulated form, a non-encapsulated form, or laminated to a particle comprising polymeric resin. Some non-limiting examples of visual effects additives are aluminum, gold, silver, copper, nickel, titanium, stainless steel, nickel sulfide, cobalt sulfide, manganese sulfide, metal oxides, white mica, black mica, pearl mica, synthetic mica, mica coated with titanium dioxide, metal-coated glass flakes, and colorants, including but not limited, to Perylene Red. The visual effect additive may have a high or low aspect ratio and may comprise greater than 1 facet. Dyes may be employed such as Solvent Blue 35, Solvent Blue 36, Disperse Violet 26, Solvent Green 3, Anaplast Orange LFP, Perylene Red, and Morplas Red 36. Fluorescent dyes may also be employed including, but not limited to, Permanent Pink R (Color Index Pigment Red 181, from Clariant Corporation), Hostasol Red 5B (Color Index #73300, CAS # 522-75-8, from Clariant Corporation) and Macrolex Fluorescent Yellow 10GN (Color Index Solvent Yellow 160:1, from Bayer Corporation). Pigments such as titanium dioxide, zinc sulfide, carbon black, cobalt chromate, cobalt titanate, cadmium sulfides, iron oxide, sodium aluminum sulfosilicate, sodium sulfosilicate, chrome antimony titanium rutile, nickel antimony titanium rutile, and zinc oxide may be employed. Visual effect additives in encapsulated form usually comprise a visual effect material such as a high aspect ratio material like aluminum flakes encapsulated by a polymer. The encapsulated visual effect additive has the shape of a bead.

The term "antistatic agent" refers to monomeric, oligomeric, or polymeric materials that can be processed into polymer resins and/or sprayed onto materials or articles to improve conductive properties and overall physical performance. Examples of monomeric antistatic agents include glycerol monostearate, glycerol distearate, glycerol tristearate, ethoxylated amines, primary, secondary and tertiary amines, ethoxylated alcohols, alkyl sulfates, alkylarylsulfates, alkylphosphates, alkylaminesulfates, alkyl sulfonate salts such as sodium stearyl sulfonate, sodium dodecylbenzenesulfonate or the like, quaternary ammonium salts, quaternary ammonium resins, imidazoline derivatives, sorbitan esters, ethanolamides, betaines, or the like, or combinations comprising at least one of the foregoing monomeric antistatic agents.

Exemplary polymeric antistatic agents include certain polyesteramides, polyether-polyamide (polyetheramide) block copolymers, polyetheresteramide block copolymers, polyetheresters, or polyurethanes, each containing polyalkylene oxide units that may be polyalkylene glycol functionality, for example, polyethylene glycol, polypropylene glycol and polytetramethylene glycol. Such polymeric antistatic agents are commercially available, such as, for example, Pelestat™ 6321 (Sanyo), Pebax™ H1657 (Atofina), and Irgastat™ P18 and P22 (Ciba-Geigy). Other polymeric materials that may be used as antistatic agents are inherently conducting polymers such as polyaniline (commercially available as PANIPOL®EB from Panipol), polypyrrole and polythiophene (commercially available from Bayer), which retain some of their intrinsic conductivity after melt processing at elevated temperatures. In one embodiment, carbon fibers, carbon nanofibers, carbon nanotubes, carbon black, or any combination of the foregoing may be used in a polymeric resin containing chemical antistatic agents to render the composition electrostatically dissipative.

Non-limiting examples of mold release compositions include esters of long-chain aliphatic acids and alcohols such as pentaerytbritol, guerbet alcohols, long-chain ketones, siloxanes, alpha.-olefin polymers, long-chain alkanes and hydrocarbons having 15 to 600 carbon atoms.

Non-limiting examples of flame retardants that can be used include potassium diphenylsulfone sulfonate, perfluoroalkane sulfonates and phosphite esters of polyhydric phenols, such as resorcinol and bisphenol A.

The thermoplastic composition may optionally comprise an impact modifier. The impact modifier may be added to the thermoplastic composition in an amount corresponding to about 1 percent to about 30 percent by weight, based on the total weight of the composition. Suitable impact modifiers include those comprising one of several different rubbery modifiers such as graft or core shell rubbers or combinations of two or more of these modifiers. Impact modifiers are illustrated by acrylic rubber ASA rubber, diene rubber, organosiloxane rubber, ethylene propylene diene monomer (EPDM) rubber, styrene-butadiene-styrene (SBS) rubber, styrene-ethylene-butadiene-styrene (SEBS) rubber, acrylonitrile-butadiene-styrene (ABS) rubber, methacrylate-butadiene-styrene (MBS) rubber, styrene acrylonitrile copolymer and glycidyl ester impact modifier.

The term "acrylic rubber modifier" may refer to multistage, core-shell, interpolymer modifiers having a crosslinked or partially crosslinked (meth)acrylate rubbery core phase, such as butyl acrylate. Associated with this crosslinked acrylic ester core is an outer shell of an acrylic or styrenic polymer, such as methyl methacrylate or styrene, which interpenetrates the rubbery core phase. Incorporation of small amounts of other monomers such as acrylonitrile or (meth)acrylonitrile within the polymer shell also provides suitable impact modifiers. The interpenetrating network is provided when the monomers forming the outer shell are polymerized and cross-linked in the presence of the previously polymerized and cross-linked (meth)acrylate rubbery phase.

Suitable impact modifiers are graft or core shell structures with a rubbery component with a Tg below 0° C., or, more specifically, −40° to −80° C., composed of poly alkylacrylates or polyolefins grafted with polymethylmethacrylate (PMMA) or styrene acrylonitrile (SAN). In one embodiment the rubber content is at least 10 wt. percent, or, more specifically, greater than 40 wt. percent, or, even more specifically 40 to 75 wt. percent.

Other suitable impact modifiers are the butadiene core-shell polymers of the type available from Rohm & Haas, for example Paraloid® EXL2600. Most suitable impact modifier will comprise a two stage polymer having a butadiene based rubbery core and a second stage polymerized from methylmethacrylate alone or in combination with styrene. Other suitable rubbers are the ABS types Blendex® 336 and 415, available from GE Specialty Chemicals. Both rubbers are based on impact modifier polymer of SBR rubber. Although several rubbers have been described, many more are commercially available. Any rubber may be used as an impact modifier as long as the impact modifier does not negatively impact the physical or aesthetic properties of the thermoplastic composition.

Non-limiting examples of processing aids that can be used include Doverlube® FL-599 (available from Dover Chemical Corporation), Polyoxyter® (available from Polychem Alloy Inc.), Glycolube® P (available from Lonza Chemical Company), pentaerythritol tetrastearate, Metablen® A-3000 (available from Mitsubishi Rayon) and neopentyl glycol dibenzoate.

Radiation stabilizers may also be present in the thermoplastic composition, specifically gamma-radiation stabilizers. Suitable gamma-radiation stabilizers include diols, such as ethylene glycol, propylene glycol, 1,3-propanediol, 1,2-butanediol, 1,4-butanediol, meso-2,3-butanediol, 1,2-pentanediol, 2,3-pentanediol, 1,4-pentanediol and 1,4-hexandiol; alicyclic alcohols such as 1,2-cyclopentanediol and 1,2-cyclohexanediol; branched acyclic diols such as 2,3-dimethyl-2,3-butanediol (pinacol), and polyols, as well as alkoxy-substituted cyclic or acyclic alkanes. Alkenols, with sites of unsaturation, are also a useful class of alcohols, examples of which include 4-methyl-4-penten-2-ol, 3-methyl-pentene-3-ol, 2-methyl-4-penten-2-ol, 2,4-dimethyl-4-pene-2-ol and 9-decen-1-ol. Another class of suitable alcohols is the tertiary alcohols, which have at least one hydroxy substituted tertiary carbon. Examples of these include 2-methyl-2,4-pentanediol (hexylene glycol), 2-phenyl-2-butanol, 3-hydroxy-3-methyl-2-butanone and 2-phenyl-2-butanol, and cycloloaliphatic tertiary carbons such as 1-hydroxy-1-methyl-cyclohexane. Another class of suitable alcohols is hydroxymethyl aromatics, which have hydroxy substitution on a saturated carbon attached to an unsaturated carbon in an aromatic ring. The hydroxy substituted saturated carbon may be a methylol group ($-CH_2OH$) or it may be a member of a more complex hydrocarbon group such as would be the case with ($-CR^{10}HOH$) or ($-CR_2^{10}OH$) wherein $R^{10}$ is a complex or a simply hydrocarbon. Specific hydroxy methyl aromatics may be benzhydrol, 1,3-benzenedimethanol, benzyl alcohol, 4-benzyloxy benzyl alcohol and benzyl alcohol. Specific alcohols are 2-methyl-2,4-pentanediol (also known as hexylene glycol), polyethylene glycol, polypropylene glycol.

Where a foam is desired, a blowing agent may be added to the thermoplastic composition. Suitable blowing agents include for example, low boiling halohydrocarbons; those that generate carbon dioxide; blowing agents that are solid at room temperature and that when heated to temperatures higher than their decomposition temperature, generate gases such as nitrogen, carbon dioxide, ammonia gas or the like, such as azodicarbonamide, metal salts of azodicarbonamide, 4,4' oxybis(benzenesulfonylhydrazide), sodium bicarbonate, ammonium carbonate, or the like, or combinations comprising at least one of the foregoing blowing agents.

Anti-drip agents may also be used, for example a fibril forming or non-fibril forming fluoropolymer such as polytetrafluoroethylene (PTFE). The anti-drip agent may be encapsulated by a rigid copolymer as described above, for example styrene-acrylonitrile copolymer (SAN). PTFE encapsulated in SAN is known as TSAN. Encapsulated fluoropolymers may be made by polymerizing the encapsulating polymer in the presence of the fluoropolymer, for example an aqueous dispersion. TSAN may provide significant advantages over PTFE, in that TSAN may be more readily dispersed in the composition. A suitable TSAN may comprise, for example, about 50 wt. percent PTFE and about 50 wt. percent SAN, based on the total weight of the encapsulated fluoropolymer. The SAN may comprise, for example, about 75 wt. percent styrene and about 25 wt. percent acrylonitrile based on the total weight of the copolymer. Alternatively, the fluoropolymer may be pre-blended in some manner with a second polymer, such as for, example, an aromatic polycarbonate or SAN to form an agglomerated material for use as an anti-drip agent. Either method may be used to produce an encapsulated fluoropolymer.

The thermoplastic compositions may be manufactured by methods generally available in the art, for example, in one embodiment, in one manner of proceeding, powdered polymer and/or other optional components are first blended, in a Henschel™ high speed mixer. Other low shear processes including but not limited to hand mixing may also accomplish this blending. The blend is then fed into the throat of a twin-screw extruder via a hopper. Alternatively, one or more of the components may be incorporated into the composition by feeding directly into the extruder at the throat and/or downstream through a sidestuffer. Such additives may also be compounded into a masterbatch with a desired polymer and fed into the extruder. The extruder is generally operated at a temperature higher than that necessary to cause the composition to flow. The extrudate is immediately quenched in a water batch and pelletized. The pellets, so prepared, when cutting the extrudate may be one-fourth inch long or less as desired. Such pellets may be used for subsequent molding, shaping, or forming.

Shaped, formed, or molded articles comprising the polycarbonate compositions are also provided. The polycarbonate compositions may be molded into useful shaped articles by a variety of means such as injection molding, extrusion, rotational molding, blow molding and thermoforming to form articles such as, for example, computer and business machine housings such as housings for monitors, handheld electronic device housings such as housings for cell phones, electrical connectors, and components of lighting fixtures, ornaments, home appliances, roofs, greenhouses, sun rooms, swimming pool enclosures and automotive application. (e.g., forward lighting enclosures for car headlamps).

The disclosure is explained in more detail with reference to the following non-limiting Examples.

EXAMPLES

Proton NMR spectra for all the starting materials and products described herein were measured using a 300 megahertz Bruker NMR spectrometer using deuterated chloroform or $Cd_6$-dimethylsulfoxide as a solvent unless otherwise specified. Compounds were further characterized by a liquid chromatograph-mass spectrometer (LC-MS) system, comprising a liquid chromatograph and a Quattro Ultima Pt mass spectrometer.

Liquid Chromatographic (LC) method was used to identity the conversion of product compound. A Xterra C18 column, length 50 meters, inner diameter 4.6 millimeters and thickness 5 micrometers was used for the analysis. The column temperature was maintained at 30° C. The column was eluted with a ratio of water to acetonitrile of 80:20. The flow rate of sample in the column was maintained at 1.00 milliliter per minute (ml/min) and the amount of sample injected was 5 micro liter. The total run time was 23 min.

Example 1

This example provides a method for the preparation of methyl-4,4'-bis(4-hydroxy-phenyl)-2,6-diphenyl-cyclohexane-1,1-dicarboxylate (Formula (I)). The method includes 3 steps as described below.

STEP A: Preparation of Dibenzalacetone (Formula (IV))

To an aqueous solution of sodium hydroxide (200 grams (g) in one liter of water) was added ethanol (1.6 liters; purity greater than 95%) and the resultant mixture was stirred well. Another mixture having acetone (29 g) and benzaldehyde (106 g) was added to this solution under stirring. A yellow colored precipitate was observed. The stirring was continued for about 15 minutes (min). Subsequently additional acetone (29 g) and benzaldehyde (106 g) were added and the mixture was stirred for another 45 min. The yellow colored precipitate was separated by filtration, washed with water (2 liters), and dried at room temperature to get 223 g of crude dibenzalacetone. Melting point of the compound was obtained as 104-106° C. This product was used in the next step without further purification.

STEP B: Preparation of methyl-2,6-diphenyl-cyclohexane-4-one-1,1-dicarboxylate (Formula (VI)). Dimethyl malonate (58 g) was added to a clear solution of dibenzalacetone (93.6 g, as prepared in STEP A) in absolute methanol (1.2 liters) and the resultant reaction mixture was stirred well. To this reaction mixture was added 5% sodium methoxide solution (20 ml) under stirring. The color of the reaction mixture is observed to change from yellow to orange color almost immediately. The stirring was then continued for another 4-6 hours at 60° C. The reaction mixture was then allowed to cool to room temperature, and left overnight. The colorless white precipitate was separated by filtration and washed with chilled methanol to get about 111 g of product. The filtrate was concentrated to 30% of its volume to recover the second crop of 12 g. Melting point of the combined product (first crop+second crop) was observed as 135° C. This material was used in the next step without purification.

STEP C: Preparation of methyl-4,4'-bis(4-hydroxy-phenyl)2,6-diphenyl-cyclohexane-1,1-dicarboxylate (Formula (I)).

A mixture of methyl-2,6-diphenyl-cyclohexane-4-one-1, 1-dicarboxylate (109.8 g; prepared in STEP B), phenol (141 g) and resorcinol (6.27 g), was heated to 60° C. in a three necked reaction flask to obtain a homogenous solution. Dry hydrogen chloride gas was purged into the reaction mixture for 12 hours and the temperature was maintained at 60° C. After 12 hours, the reaction mixture was allowed to attain room temperature over a period of 2 to 3 hours. At the end of this time, white precipitate was observed in the reaction flask. Toluene (200 ml) was added to the reaction mixture and stirred for about 30 minutes and the resultant mixture was filtered. The filter cake obtained was triturated with 1.5 liters of 1:1 mixture of toluene and petroleum ether and stirred for about 15 minutes. The solid was filtered and dried to get a yellow cake which was further suspended in hot water (500 ml), stirred for about 5 minutes and filtered again. The obtained solid was crystallized with isopropanol to get a crystalline white methyl-4,4'-bis(4-hydroxy-phenyl)-2,6-diphenyl-cyclohexane-1,1-dicarboxylate with a yield of about 101 g and having a melting point greater than 270° C. The solid was dissolved in deuterated chloroform and analyzed using NMR. The corresponding peaks obtained were at δ 2.35-2.73 (4H, m, $CH_2$), 3.0-3.2 (6H, s, $OCH_3$), 3.25-3.75 (2H, br-s, OH), 4.26-4.52 (2H, m, CH), 6.68-6.81 (4H, dd, Ar—H), 6.97-7.07 (4H, dd, Ar—H), 7.16-7.4 (10H, m, Ar—H).

Example 2

Preparation of methyl-1-cyano-4,4'-bis(4-hydroxy-phenyl) 2,6-diphenyl-cyclohexane-1-carboxylate (Formula (I)).

STEP I: Cyanoethyl acetate (13.3 g) and Triton®-B (Benzyltriethylammonium hydroxide); 20-22 drops) were added to a suspension of dibenzalacetone (25.0 g; as prepared in step A of example I above) in absolute ethanol (200 cc) and the resultant mixture was stirred well. A clear solution was obtained which immediately changed to a thick white precipitate. Ethanol (150 cc) was added to the reaction mass and stirred well for about 1-2 hours at 0° C. The colorless precipitate obtained was separated by filtration, washed with chilled ethanol to obtain 22.3 g of methyl-1-cyano-2,6-diphenyl-cyclohexane-4-one-1,1-carboxylate having a melting point of about 133-138° C. This material was used in step II without purification. The solid was analyzed using NMR (Acetone-$D_6$). The corresponding peaks were at δ 0.70-0.78 (3H, t), 2.65-3.05 (4H, m), 3.45-4.17 (4H, m), 7.32-7.45 (10H, br-s).

Step II: A mixture of methyl-1-cyano-2,6-diphenyl-cyclohexane-4-one-1,1-carboxylate (34.8 g; as prepared in step I), phenol (47 g) and resorcinol (2.05 g), was heated to 60° C. in a three necked reaction flask until a homogenous solution was obtained. Dry hydrogen chloride gas was passed into the reaction mixture for 12 hours maintaining the temperature at 60° C. After 12 hours, the reaction mixture was allowed to attain room temperature and during this period formation of white precipitate was observed. Toluene (100 ml) was added to the reaction mixture and the reaction mixture stirred for 30 minutes. The resultant solid was filtered. The solid cake was triturated with 500 ml of 1:1 mixture of toluene and petroleum ether and the resultant mixture stirred for about 15 minutes. The mixture was filtered. The filter cake on drying provided a yellow cake which was further suspended in hot water (500 ml, temperature 70° C.), stirred for about 15 minutes and filtered again. The resultant solid was crystallized with isopropanol to get a crystalline white solid weighing 36.3 g, having a melting point greater than 250° C. The solid was dissolved in deuterated acetone and analyzed using NMR. The corresponding peaks were at δ 0.70-0.78 (3H, t), 2.65-3.05 (4H, m), 3.45-4.17 (4H, m), 6.74-6.85 (4H, dd), 7.05-7.15 (4H, dd), 7.32-7.45 (10H, br-s), 8.23 (2H.br-s).

As can be seen from the foregoing examples a compound having Formula (I) can be readily prepared as shown in Examples 1 and 2.

For the examples below unless indicated otherwise temperature is in degrees centigrade (° C.). Molecular weights are reported as number average (Mn) or weight average (Mw) molecular weight and were determined by gel permeation chromatography using polymer solutions comprising the product copolycarbonates at a concentration of about 1 milligram (mg) per milliliter (ml) in methylene chloride ($CH_2Cl_2$). The molecular weights are referenced to polystyrene (PS) molecular weight standards or polycarbonate (PC) standards as referred to in the examples. Copolycarbonate composition was determined by NMR spectroscopic analysis. Glass transition temperature (Tg) values were determined by differential scanning calorimetry, using a Perkin Elmer DSC7. The Tg was calculated, based on the "½ Cp" (half centipoises) method (heat capacity at constant pressure), using a heating ramp of 20° C./minute. The second heating curve is used for the actual Tg determination.

Examples 3-6

The general method employed for the preparation of copolymer using BPA and methyl-4,4-Bis(4-hydroxyphenyl)-2,6-diphenyl cyclohexane-1,1-dicarboxylate is outlined below. The melt reactor was prepared by acid washing, rinsing and drying with nitrogen gas. The melt reactor was then charged with BPA, methyl-4,4-bis(4-hydroxyphenyl)-2,6-diphenyl cyclohexane-1,1-dicarboxylate, bismethylsalicylate (bMSC) in examples 1 to 3 and diphenyl carbonate (DPC) in example 4, and 100 microliters of an aqueous solution of tetramethyl ammonium hydroxide (TMAH) and sodium hydroxide (NaOH) in an amount corresponding to about $2.5 \times 10^{-5}$ TMAH and $2 \times 10^{-6}$ moles NaOH based on the total number of moles of BPA and methyl-4,4-bis(4-hydroxyphenyl)-2,6-diphenyl cyclohexane-1,1-dicarboxylate (MBHDCD) combined. The amounts of reactants are included in Table 1 below.

TABLE 1

| Example | BPA (grams) | MBHDCD | bMSC (g) |
|---|---|---|---|
| 3 | 12.26 | 3.2 | 20 |
| 4 | 6.81 | 15.99 | 20 |
| 5 | 0 | 16.07 | 10 |
| 6 | 4.93 | 11.58 | 10[1] |

[1] diphenyl carbonate

After the melt reactor was purged with nitrogen, a temperature-pressure regime of specific time intervals involving certain number of steps was used to carry out the melt polymerization. The number of steps, the corresponding time, temperature and pressure at each step is outlined in Table 2 (Examples 3 and 4), Table 3 (Example 5) and Table 4 (Example 6) below.

TABLE 2

| Steps | Time (minutes) | Temperature (° C.) | Pressure (millibars) | Pressure (Pascals) |
|---|---|---|---|---|
| 1 | 10 | 200 | 1010 | $10.1 \times 10^4$ |
| 2 | 5 | 220 | 1010 | $10.1 \times 10^4$ |
| 3 | 30 | 220 | 500 | $5 \times 10^4$ |
| 4 | 5 | 270 | 500 | $5 \times 10^4$ |
| 5 | 10 | 300 | 0.5-1 | 50-100 |

TABLE 3

| Steps | Time (minutes) | Temperature (° C.) | Pressure (millibars) | Pressure (Pascals) |
|---|---|---|---|---|
| 1 | 7 | 200 | 1010 | $10.1 \times 10^4$ |
| 2 | 7 | 230 | 1010 | $10.1 \times 10^4$ |
| 3 | 5 | 250 | 500 | $5 \times 10^4$ |
| 4 | 5 | 270 | 500 | $5 \times 10^4$ |
| 5 | 2 | 300 | 100 | $1 \times 10^4$ |
| 6 | 5 | 350 | 100 | $1 \times 10^4$ |
| 7 | 2 | 370 | 100 | $1 \times 10^4$ |
| 8 | 10 | 370 | 0.5-1 | 50-100 |

TABLE 4

| Steps | Time (minutes) | Temperature (° C.) | Pressure (millibars) | Pressure (Pascals) |
|---|---|---|---|---|
| 1 | 10 | 230 | 1010 | $10.1 \times 10^4$ |
| 2 | 60 | 230 | 170 | $1.7 \times 10^4$ |
| 3 | 25 | 270 | 20 | $2.0 \times 10^4$ |
| 4 | 5 | 330 | 20 | $2.0 \times 10^4$ |
| 5 | 10 | 330 | 0.5-1 | 50-100 |
| 6 | 20 | 350 | 0.5-1 | 50-100 |

As the reaction progressed through the different steps, corresponding by-products were removed from the reaction mixture by distillation; for example in Examples 3-5 where bMSC was employed as the carbonylating agent, methyl salicylate was removed as the byproduct, and in Example 6 where DPC was used as the carbonylating agent, phenol was removed as the byproduct. A fast increase in the torque build up was observed during the polymerization. After the specified number of steps in each example, the reactor was brought back to atmospheric pressure with nitrogen flow, and the product copolycarbonate was recovered and analyzed. The results of the analysis are included in Table 5 below.

TABLE 5

| Examples | Tg ° C. | Mw Daltons | Refractive Index |
|---|---|---|---|
| 1 | 152 | 43,200 | NA |
| 2 | 215 | NA | 1.58 |
| 3 | 251 | 18,000 | NA |
| 4 | 233 | 47,000 | NA |

NA → not available

The results provided in Table 5 indicate that by employing the polycyclic dihydroxy aromatic compounds prepared in Example 3, a polymer having a Tg greater than 150° C. and Refractive Index of 1.58 is obtained. The examples indicate that polycyclic dihydroxy compound may be employed to prepare polymers with great ease using an interfacial or a melt process as discussed above. More over the Tg and Refractive index values indicate that the polymer may have high heat optical applications.

Example 7

Dichloromethane (250 milliliters (ml)), deionized water (250 ml), 4,4-bis-(4-hydroxyphenyl)-2,6-diphenyl-cyclohexane-1,1-dicarboxylic acid dimethyl ester (21.05 grams (g); 0.039 moles), Bisphenol A (8.95 g; 0.039 moles), p-cumylphenol (0.50 g, 0.0024 moles), and triethylamine (0.16 ml; 0.0011 moles) were charged to a 2 L flask equipped with mechanical agitation, a condenser, and a caustic vent scrubber. Phosgene (12 g, 0.12 moles) was added at a rate of 1.0 g/minutes with vigorous stirring while a 50 wt percent solution of sodium hydroxide was added at a rate to maintain the pH of the reaction mixture at about 9 to 10. After the addition of phosgene was completed, the reaction mixture was purged with nitrogen for about 10 minutes to ensure complete removal of phosgene. Stirring was stopped, and the reaction mass allowed to phase separate. A small amount of solids were visible at the phase interface. The organic phase containing the product polymer was separated, washed with 1N HCl (1×500 ml) and then with DI water (3×500 ml). The polymer solution was then slowly fed into approximately 2 L of hot water with rapid stirring to boil off the dichloromethane, and the resulting white polymer was isolated by filtration and dried in air at 110° C. overnight. GPC of the dried polymer gave Mw=16659 and Mn=6758 using polycarbonate standard. Tg of the polymer 232° C.

Example 8

Dichloromethane (400 ml), deionized water (400 ml), 4,4-bis-(4-hydroxyphenyl)-2,6-diphenyl-cyclohexane-1,1-dicarboxylic acid dimethyl ester 34.0 g, Bisphenol A (14.15 g), and methyltributylammonium chloride (0.2 ml of a 70 wt percent aqueous solution) were charged to a 2 L flask equipped with mechanical agitation, condenser, and a caustic vent scrubber. Phosgene (18 g) was added at a rate of 1.0 g/minute with vigorous stirring while a 50 wt percent solution of sodium hydroxide was added at a rate to maintain the pH of the reaction mixture at about 6 to 7. After phosgene addition was complete, nitrogen was purged through the reaction mixture and the reaction mixture was stirred until all solids disappeared. A 50 wt percent solution of sodium hydroxide was added as needed to maintain the pH at about 7 to 8. Triethylamine (approx 0.1 ml) was then added and a 50 wt percent solution of sodium hydroxide was added (as needed) to maintain the pH at about 9 to 10, until no chloroformates were detected. The nitrogen purge was stopped and additional phosgene (2 g) was added at a rate of 1 g/min while a 50 wt percent solution of sodium hydroxide was added at a rate to maintain the at about 9 to 10. After phosgene addition was complete, the batch was purged with nitrogen for about 10 minutes to ensure complete removal of phosgene. Stirring was stopped, and the batch allowed to phase separate. The organic phase containing polymer was separated, washed with 1N HCl (1×500 ml) and then with deionized water (3×500 ml). The polymer solution was then slowly fed into approximately 2 L of hot water with rapid stirring to boil off the $CH_2Cl_2$, and the resulting white polymer was isolated by filtration and dried in air at 110° C. overnight. GPC of the dried polymer gave Mw=55473 and Mn=17080 using polycarbonate standard. Tg of the polymer=232° C.

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

What is claimed is:

1. A process for preparing a polymer, comprising reacting acetone with a compound of Formula (III) in the presence of a first catalyst to produce dibenzalacetone of Formula (IV)

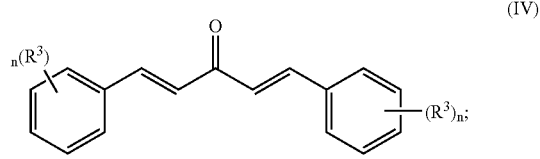

reacting the dibenzalacetone of Formula (IV) in the presence of a second catalyst with a compound of Formula (V) to produce a compound of Formula (VI)

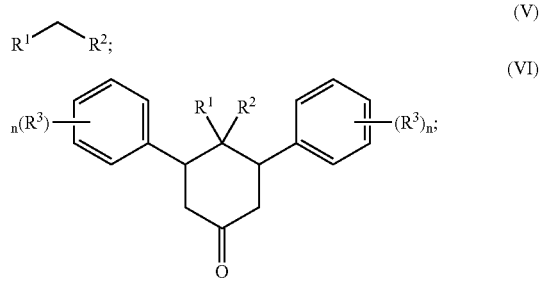

reacting the compound of Formula (VI) with a compound of Formula (VII) in the presence of an acid catalyst and a promoter to produce a compound of Formula (I),

-continued

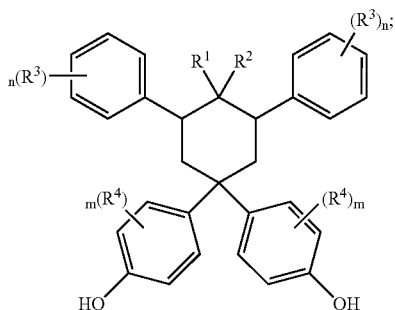

(I)

wherein $R^1$ is selected from the group consisting of a cyano functionality, a nitro functionality, an aliphatic functionality having 1 to 10 carbons, an aliphatic ester functionality having 2 to 10 carbons, a cycloaliphatic ester functionality having 4 to 10 carbons and an aromatic ester functionality having 4 to 10 carbons; $R^2$ is selected from the group consisting of a cyano functionality, a nitro functionality, an aliphatic ester functionality having 2 to 10 carbons, a cycloaliphatic ester functionality having 4 to 10 carbons and an aromatic ester functionality having 4 to 10 carbons; and each $R^3$ and $R^4$, at each occurrence, can be the same or different and are independently at each occurrence an aliphatic functionality having 1 to 10 carbons or a cycloaliphatic functionality having 3 to 10 carbons; "n" is an integer having a value 0 to 4 and "m" is an integer having a value 0 to 4; and polymerizing the compound of Formula (I).

2. The process of claim 1, wherein polymerizing comprises dissolving or dispersing a polycyclic dihydroxy compound of Formula (I) in an aqueous base, adding the resulting mixture to a water-immiscible solvent to form an interfacial mixture, and contacting the interfacial mixture with a carbonate precursor in the presence of a catalyst under controlled pH conditions.

3. The process of claim 2, wherein the aqueous base comprises sodium hydroxide or potassium hydroxide.

4. The process of claim 2, wherein the carbonate precursor comprises a carbonyl halide, a haloformate, bishaloformate of a glycol, an ester or mixtures of at least two or more of the foregoing.

5. The process of claim 2, wherein the catalyst comprises triethylamine or a phase transfer catalyst or a combination of triethylamine and a phase transfer catalyst.

6. The process of claim 2, wherein the water-immiscible solvent comprises methylene chloride, 1,2-dichloroethane, chlorobenzene, toluene or a combination of two or more of the foregoing solvents.

7. The process of claim 2, wherein pH is maintained at a pH of about 8 to about 10.

8. The process of claim 1, wherein the polymerizing comprises reacting, in a molten state, the polycyclic dihydroxy compound of Formula (I) and a diaryl carbonate ester, in the presence of a transesterification catalyst.

9. The process of claim 8, wherein the diaryl carbonate ester comprises a diphenylcarbonate ester, bismethyl salicylate carbonate or a combination of diphenylcarbonate ester and bis methyl salicylate carbonate.

10. The process of claim 1, wherein said polymerizing comprises reacting a dihydroxy compound of Formula (I) with a dicarboxylic acid compound of Formula (XVII)

(XVII)

wherein $R^8$ is independently at each occurrence hydroxy, chloro, or $OR^9$, wherein $R^9$ is independently at each occurrence selected from the group consisting of an aliphatic functionality having 1 to 10 carbons, a cycloaliphatic functionality having 3 to 10 carbons, and an aromatic functionality having 6 to 10 carbons; and wherein "T" is a divalent functionality derived from a dicarboxylic acid, wherein the divalent functionality comprises a cycloaliphatic functionality having 6 to 10 carbon atoms, an aromatic functionality having 6 to 20 carbon atoms, or an aliphatic functionality having 2 to 10 carbon atoms.

11. The process of claim 1, wherein said polymerizing comprises reacting a dihydroxy compound of Formula (I) with a carbonate precursor and a dicarboxylic acid compound of Formula (XVII)

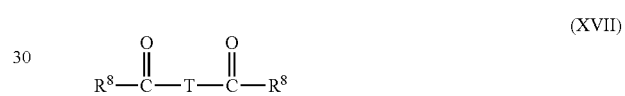

(XVII)

wherein $R^8$ is independently at each occurrence hydroxy, chloro, or $OR^9$, wherein $R^9$ is independently at each occurrence selected from the group consisting of an aliphatic functionality having 1 to 10 carbons, a cycloaliphatic functionality having 3 to 10 carbons, and an aromatic functionality having 6 to 10 carbons; and wherein "T" is a divalent functionality derived from a dicarboxylic acid, wherein the divalent functionality comprises a cycloaliphatic functionality having 6 to 10 carbon atoms, an aromatic functionality having 6 to 20 carbon atoms, or an aliphatic functionality having 2 to 10 carbon atoms.

12. A process for preparing a polymer, comprising reacting acetone with benzaldehyde having Formula (VIII) in presence of sodium hydroxide to produce dibenzalacetone having Formula (IX)

(VIII)

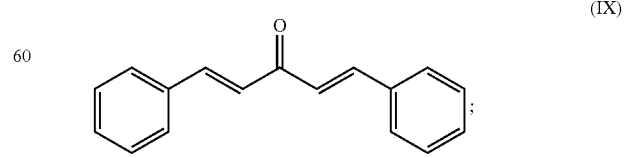

(IX)

reacting the dibenzalacetone having Formula (IX) in presence of sodium methoxide with dimethyl malonate having Formula (X) to produce methyl-2,6-diphenyl-cyclohexane-4-one-1,1-dicarboxylate having Formula (XI)

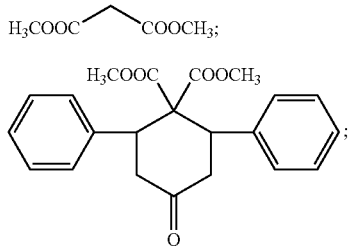

reacting methyl-2,6-diphenyl-cyclohexane-4-one-1,1-dicarboxylate with phenol having Formula (XII) in presence of an acid catalyst and a promoter to produce methyl-4,4'-bis(4-hydroxy-phenyl)-2,6-diphenyl-cyclohexane-1,1-dicarboxylate having Formula (II),

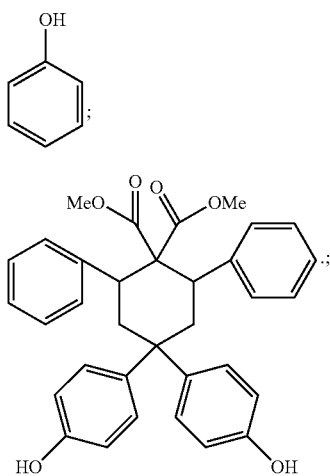

and
polymerizing the compound of Formula (II).

13. The process of claim 12, wherein polymerizing comprises
dissolving or dispersing a polycyclic dihydroxy compound of Formula (I) in an aqueous base,
adding the resulting mixture to a water-immiscible solvent to form an interfacial mixture, and
contacting the interfacial mixture with a carbonate precursor in the presence of a catalyst under controlled pH conditions.

14. The process of claim 13, wherein the aqueous base comprises sodium hydroxide or potassium hydroxide.

15. The process of claim 13, wherein the carbonate precursor comprises a carbonyl halide, a haloformate, bishaloformate of a glycol, an ester or mixtures of at least two or more of the foregoing.

16. The process of claim 13, wherein the catalyst comprises triethylamine or a phase transfer catalyst or a combination of triethylamine and a phase transfer catalyst.

17. The process of claim 13, wherein the water-immiscible solvent comprises methylene chloride, 1,2-dichloroethane, chlorobenzene, toluene or a combination of two or more of the foregoing solvents.

18. The process of claim 13, wherein pH is maintained at a pH of about 8 to about 10.

19. The process of claim 12, wherein the polymerizing comprises reacting, in a molten state, the polycyclic dihydroxy compound of Formula (I) and a diaryl carbonate ester, in the presence of a transesterification catalyst.

20. The process of claim 19, wherein the diaryl carbonate ester comprises a diphenylcarbonate ester, bismethyl salicylate carbonate or a combination of diphenylcarbonate ester and bis methyl salicylate carbonate.

21. The process of claim 12, wherein said polymerizing comprises
reacting a dihydroxy compound of Formula (I) with a dicarboxylic acid compound of Formula (XVII)

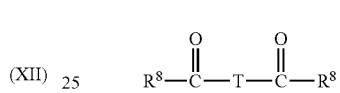

wherein $R^8$ is independently at each occurrence hydroxy, chloro, or $OR^9$, wherein $R^9$ is independently at each occurrence selected from the group consisting of an aliphatic functionality having 1 to 10 carbons, a cycloaliphatic functionality having 3 to 10 carbons, and an aromatic functionality having 6 to 10 carbons; and wherein "T" is a divalent functionality derived from a dicarboxylic acid, wherein the divalent functionality comprises a cycloaliphatic functionality having 6 to 10 carbon atoms, an aromatic functionality having 6 to 20 carbon atoms, or an aliphatic functionality having 2 to 10 carbon atoms.

22. The process of claim 12, wherein said polymerizing comprises
reacting a dihydroxy compound of Formula (I) with a carbonate precursor and a dicarboxylic acid compound of Formula (XVII)

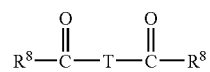

wherein $R^8$ is independently at each occurrence hydroxy, chloro, or $OR^9$, wherein $R^9$ is independently at each occurrence selected from the group consisting of an aliphatic functionality having 1 to 10 carbons, a cycloaliphatic functionality having 3 to 10 carbons, and an aromatic functionality having 6 to 10 carbons; and wherein "T" is a divalent functionality derived from a dicarboxylic acid, wherein the divalent functionality comprises a cycloaliphatic functionality having 6 to 10 carbon atoms, an aromatic functionality having 6 to 20 carbon atoms, or an aliphatic functionality having 2 to 10 carbon atoms.

* * * * *